(12) United States Patent
Stoeber et al.

(10) Patent No.: US 8,512,716 B2
(45) Date of Patent: Aug. 20, 2013

(54) DIAGNOSTIC, PREDICTIVE AND PROGNOSTIC TESTING FOR CANCER

(75) Inventors: Kai Stoeber, Ely (GB); Gareth Hayden Williams, Ely (GB)

(73) Assignee: Cambridge Cancer Diagnostics Limited, Cambridgeshire (GB)

( * ) Notice: Subject to any disclaimer, the term of this patent is extended or adjusted under 35 U.S.C. 154(b) by 168 days.

(21) Appl. No.: 12/738,062

(22) PCT Filed: Oct. 15, 2008

(86) PCT No.: PCT/GB2008/003501
§ 371 (c)(1),
(2), (4) Date: Jul. 26, 2010

(87) PCT Pub. No.: WO2009/050461
PCT Pub. Date: Apr. 23, 2009

(65) Prior Publication Data
US 2010/0285474 A1    Nov. 11, 2010

(30) Foreign Application Priority Data

Oct. 15, 2007 (GB) .................................. 0720113.0

(51) Int. Cl.
*A61K 38/00* (2006.01)
*A61K 35/12* (2006.01)

(52) U.S. Cl.
USPC ........................................ 424/277.1; 514/1.1

(58) Field of Classification Search
None
See application file for complete search history.

(56) References Cited

U.S. PATENT DOCUMENTS

2004/0146513 A1   7/2004  Gerdes et al.
2005/0260653 A1*  11/2005 Labaer et al. ................... 435/6
2007/0128599 A1   6/2007  Ridder et al.

OTHER PUBLICATIONS

Dudderidge et al, British J Can 96:1384-1393, 2007.*
Shapiro et al, J Clin Invest 104:1645-1653. 1999.*
Shetty et al, British J Can 93:1295-1300, 2005, IDS May 12, 2010, R9.*
Scott et al, Brit J Can 90:1583-1590, 2004, IDS, May 12, 2010, R8.*
Ananthanarayanan, V. et al. "Alteration of proliferation and apoptotic markers in normal and premalignant tissue associated with prostate cancer" *BMC Cancer*, Mar. 17, 2006, 6:73, pp. 1-9.
Endl, E. et al. "The expression of Ki-67, MCM3, and p27 defines distinct subsets of proliferating, resting, and differentiated cells" *Journal of Pathology*, 2001, 195:457-462.
Going, J.J. et al. "Aberrant expression of minichromosome maintenance proteins 2 and 5, and Ki-67 in dysplastic squamous oesophageal epithelium and Barrett's mucosa" *Gut*, 2002, 50:373-377.
Korkolopoulou, P. et al. "Minichromosome maintenance proteins 2 and 5 expression in muscle-invasive urothelial cancer: a multivariate survival study including proliferation markers and cell cycle regulators" *Human Pathology*, 2005, 36:899-907.
Li, Y. et al. "Transcriptional changes associated with breast cancer occur as normal human mammary epithelial cells overcome senescence barriers and become immortalized" *Molecular Cancer*, Jan. 2007, 6:7, pp. 1-17.
Loddo, M. et al. "Cell-cycle-phase progression analysis identifies unique phenotypes of major prognostic and predictive significance in breast cancer" *British Journal of Cancer*, 2009, 100:959-970.
Padmanabhan, V. et al. "DNA replication regulation protein Mcm7 as a marker of proliferation in prostate cancer" *J Clin Pathol*, 2004, 57:1057-1062.
Scott, I.S. et al. "A novel immunohistochemical method for estimating cell cycle phase distribution in ovarian serous neoplasms: implications for the histopathological assessment of paraffin-embedded specimens" *British Journal of Cancer*, 2004, 90:1583-1590.
Shetty, A. et al. "DNA replication licensing and cell cycle kinetics of normal and neoplastic breast" *British Journal of Cancer*, 2005, 93:1295-1300.
Swords, R. et al. "Cdc7 kinase—A new target for drug development" *European Journal of Cancer*, 2010, 46:33-40.
Williams, G.H. et al. "Cell cycle markers in clinical oncology" *Current Opinion in Cell Biology*, 2007, 19:672-679.
Yang, J. et al. "Prognostic significance of MCM2, Ki-67 and gelsolin in non-small cell lung cancer" *BMC Cancer*, 2006, 6:203, pp. 1-10.

* cited by examiner

*Primary Examiner* — Lei Yao

(74) *Attorney, Agent, or Firm* — Saliwanchik, Lloyd & Eisenschenk

(57) ABSTRACT

The present invention relates to a method for determining a prognosis of progression of a cancer in a subject, a method for determining a treatment protocol for a subject having cancer or a method for determining efficacy of a therapeutic treatment of a subject, the method comprising the steps of:
  (a) assessing a level of a first biomarker selected from at least one of Mcm2-7 in a biological sample from the subject: and
  (b) assessing the level of a second biomarker selected from at least one of geminin, Aurora A, Plk1, Ki67 and H3S10ph in the biological sample from the subject, wherein the combination of the level of the first biomarker compared to a pre-determined value and the level of the second biomarker compared to a predetermined value is indicative of cancer progression in the subject or is indicative of the treatment regimen prescribed for the subject or is indicative of the efficacy of the therapeutic treatment.

11 Claims, 17 Drawing Sheets

DIAGNOSTIC, PREDICTIVE AND PROGNOSTIC TESTING FOR CANCER

CROSS-REFERENCE TO RELATED APPLICATION

This application is the U.S. national stage application of International Patent Application No. PCT/GB2008/003501, filed Oct. 15, 2008, the disclosure of which is hereby incorporated by reference in its entirety, including all figures, tables and amino acid or nucleic acid sequences.

FIELD OF INVENTION

The present invention relates generally to the field of cancer. In particular, the present invention relates to cancer prognostic and treatment protocols.

BACKGROUND

The majority of cells in the human body reside in non-proliferating, out-of-cycle states and only a minority population is actively cycling. These cycling cells are mainly located in stem-transit amplifying compartments of self-renewing tissues such as cervix, colon or skin. In contrast, most functional cells (e.g. hepatocycles) reside in a quiescent (G0), reversibly arrested state, or have irreversibly withdrawn from the mitotic cell division cycle into terminally differentiated states (e.g. neurons, myocytes, or surface colonic epithelial cells). Cancers, on the contrary, are characterized by uncontrolled cell growth and therefore contain a high proportion of cycling cells.

Cells are responsive to mitogens in their environment at a discrete time in G1, referred to as the restriction point. The absence of mitogens does not affect cell cycle progression through S, G2 and M phase until cells return to their sensitive window in G1. In response to high cell density or mitogen deprivation, cells accumulate with a 2N DNA content and exit into G0. The cell cycle phase transitions are driven by changes in cyclin-CDK pairs. Cyclin D-CDK4, cyclin D-CDK6 and cyclin E-CDK2 regulate G0/G1 and are required for full E2F activity, S phase is initiated by cyclinA-CDK2, and cyclin B-CDK1 regulates progression through G2 and entry into mitosis. What distinguishes cells in out-of-cycle states from cells engaged in cycle remains to be elucidated.

Cancer is a complex group of heterogeneous diseases caused by the accumulation of gene mutations, which increase the activity of regulatory genes that stimulate cell proliferation and decrease the activity of proteins that normally restrain it. Activation of dominant stimulatory oncogenes or inactivation of recessive tumour suppressor genes, through point mutation, gene amplification, hypermethylation, translocation, or interaction with viral oncoproteins, can affect all levels of growth signalling pathways including mitogens, mitogen growth factor receptors, Ras, Raf, ABL, PI3 kinase AKt upstream to molecules such as p16INK4A, Myc, cyclin D, cyclin E, pRB and p53 downstream.

Microarray gene expression profiling is ideally suited for analysis of the complex multifactorial, interactive and stepwise alterations in gene expression that characterise tumourigenesis and is currently an intensive area of investigation aimed at identifying unique molecular signatures that can be exploited for cancer diagnosis and prognosis. Interestingly, the expression arrays include a proliferation signature, genes whose expression pattern correlates with tumour grade (differentiation status), cell cycle status and doubling times. This proliferation signature is one of the most prominent gene-expression patterns observed in tumour datasets, regardless of the tissue from which it is derived and includes many cell cycle regulated genes such as E2F1, BUB1, PLK1, cyclins E1, D1 and B1.

Unfortunately, the actual performance of prediction rules using gene expression has not turned out to be as informative as initially suggested for many tumour types and the list of genes identified can be highly unstable. For example, most predictive rules using gene expression have not provided a significantly improved prognostic classification for breast cancer when compared to conventional clinicopathological criteria such as tumour differentiation status, extent of spread and proliferation index. Indeed, many of the published gene signatures predicting distant-metastasis free survival in cancers have been found to correlate significantly with differentiation status.

The global microarray approach for identification of clinically useful proliferation signatures is potentially constrained. Firstly, the microarray approach in some part assumes a single compartment tumour model, in which cancers are composed of proliferating, exponentially growing cells. Neoplasms, however, are highly heterogeneous with regard to the cell cycle state of individual tumour cells. For example, in well-differentiated, low-grade tumours only a very small fraction of clonogenic tumour cells may be cycling, but in which the majority have executed their differentiation programmes and irreversibly withdrawn from cycle into a differentiated state (sterile compartment). Thus benign hyperproliferative conditions (e.g. hyperplasia) and physiological reparative growth, reactive pathological conditions containing large numbers of mitotic cells, may give higher proliferation signatures than well-differentiated cancers.

Secondly, tumour cells in vivo might also withdraw reversibly from cycle into a non-proliferating G0 state. Indeed, in many tumours the non-proliferating cells are the majority; that is the growth fraction (the ratio of proliferating to total cells) is less than 0.5. This situation is perhaps not surprising, because normal tissues are composed of mixed proliferating and non-proliferating elements and some remnant of this complex behaviour is hardwired into most cancers. The presence of contaminating benign neoplastic cells, tumour stroma, lymphoid follicles, intra- and peri-tumoural inflammatory infiltrates, and other connective tissues such as blood vessels also distorts the analysis by adding large numbers of cells with additional complex cell cycle kinetics. Hence the complex and heterogeneous cell cycle kinetics within individual tumours are likely to hinder identification of clinically useful microarray proliferation signatures, a problem that has also constrained the use of flow cytometry in routine clinical practice.

The use of flow cytometry has also had a limited impact since clinical samples are often not suitable for such analysis. This is partly due to fixation artifacts, inadequate amounts of tissue, and because of interpretation difficulties due to contaminating populations from reactive stroma and/or benign elements.

Assessment of cell proliferation markers has not previously provided any prognostic and predictive solution, and experts in the field have been sceptical that proliferation markers will provide useful clinical information. There is a belief that measuring parameters of cell proliferation will provide objective information about tumours, but despite numerous studies there is little direct evidence that the use of certain cell proliferation markers are really an improvement on conventional histological assessment optimally employed. Few studies have even addressed the critical issue of the relative value of proliferation markers compared to the standard histopathological grading and staging.

While gene expression has been applied to predicting the outcome in cancers, the actual performance of prediction rules using gene expression has not turned out to be as informative as initially suggested. For example, currently most predictive rules using gene expression have not provided a significantly improved prognostic classification when compared to the conventional NPI prognostic factors in breast cancer. The identification of new biomarkers to improve prognostic assessment in common cancers is therefore urgently required.

Breast cancer is an example of a common cancer and is a complex disease due to its morphological and biological heterogeneity, its tendency to acquire chemo-resistance and the existence of several molecular mechanisms underlying its pathogenesis. Half of women who receive loco-regional treatment for breast cancer will never relapse, whereas the other half will eventually die from metastatic disease. It is therefore imperative to distinguish clearly between these two groups of patients for optimal clinical management. Unfortunately, prognostic markers for breast cancers are at present limited. There is also lack of a test (predictive test) which allows selection of the most appropriate anti-cancer drugs particularly in the context of the new generation of small molecule inhibitors that target critical kinases involved in growth control and cell cycle transitions. For example in breast cancer predictive testing is presently limited to Her2 immunoexpression profiling.

Epithelial ovarian carcinoma (EOC) is another common cancer and is the fourth most common cancer in women in the U.S. and the U.K. Patients often presents with advanced disease, and despite improvements in drug therapy, survival is poor. At present, tumour stage is the most important prognostic factor. Residual disease after surgery, histologic subtype, and tumour grade also predict survival, but give little information about the biological variables responsible for stage progression and outcome.

Their remains a need for improved diagnostic, prognostic and predictive approaches to diseases caused by abnormal proliferation, such as cancerous or pre-cancerous conditions.

The present invention is directed to alleviating at least one disadvantage associated with the prior art.

Any discussion of documents, devices, acts or knowledge in this specification is included to explain the context of the invention. It should not be taken as an admission that any of the material forms a part of the prior art base or the common general knowledge in the relevant art on or before the priority date of the disclosure and claims herein.

SUMMARY OF INVENTION

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In a first aspect, the present invention provides a method of determining the presence or absence of abnormally proliferating cells or cellular growth abnormality in a body sample from an individual, the method including detecting in the sample a biomarker, wherein the biomarker is selected from group consisting of DNA replication licensing factors, Aurora kinases, Ki67, geminin, Polo-like kinases, and their substrate Histone H3 (referred to as "H3S10ph" hereinafter) and combinations thereof.

In one embodiment, the biomarker is detected using a specific binding member directed against a target polypeptide of the biomarker.

In a second aspect, the present invention provides a method of categorising a tissue as (i) normal or (ii) potentially or actually pre-cancerous or cancerous, dysplastic or neoplastic, the method including determining binding to a sample of the tissue of a specific binding member directed against a biomarker, wherein the biomarker is selected from group consisting of DNA replication licensing factors, Aurora kinases, Ki67, geminin, Polo-like kinases, H3S10 ph and combinations thereof.

In one embodiment, the specific binding member is directed against a target polypeptide of the biomarker.

In one embodiment, the pattern or degree of binding may be compared with that for a known normal sample and/or a known abnormal sample.

In one embodiment, the ratio of one biomarker versus a further biomarker is determined.

In a third aspect, the present invention provides a method of marking abnormal cells within a tissue sample, the method including contacting the sample with a specific binding member directed against a target polypeptide, wherein the target polypeptide is selected from group consisting of DNA replication licensing factors, Aurora kinases, Ki67, geminin, Polo-like kinases, H3S10ph, and combinations thereof, under conditions wherein the specific binding member binds to abnormally proliferating cells and not normal cells.

In a fourth aspect, the present invention provides the use of a specific binding member directed against a target polypeptide, for determining, assessing or diagnosing the presence or absence of abnormal cellular proliferation, cellular growth abnormality, tumour cell cycle kinetics, cell cycle phase distribution, dysplasia, neoplasia, or a potentially or actually pre-cancerous or cancerous state in a tissue or sample thereof.

In one embodiment, the target polypeptide comprises two or more markers selected from the group comprising DNA replication licensing factors, Aurora kinases, Ki67, geminin, Polo-like kinases, H3S10ph and combinations thereof.

In a fifth aspect, the present invention provides a method of predicting response to therapy or predicting disease progression in a cancer, the method comprising determining the presence or absence of abnormally proliferating cells or cellular growth abnormality in a body sample from an individual, the method including detecting in the sample a target polypeptide, wherein the target polypeptide is selected from group consisting of DNA replication licensing factors, Aurora kinases, Ki67, geminin, Polo-like kinases, H3S10ph and combinations thereof.

In a sixth aspect, the present invention provides a method of monitoring response to therapy drug development studies, the method comprising detecting in a body sample a biomarker, wherein the biomarker is selected from group consisting of DNA replication licensing factors, Aurora kinases, Ki67, geminin, Polo-like kinases, and H3S10ph and combinations thereof, assessing the biomarker expression to determine the presence or absence of abnormal cellular proliferation, cellular growth abnormality, tumour cell cycle kinetics, cell cycle phase distribution, dysplasia, neoplasia, or a potentially or actually pre-cancerous or cancerous state in the sample.

In one embodiment, the drug development studies are pre-clinical drug development studies.

In one embodiment, the drug development studies are pre-clinical drug development studies.

In some embodiments, the preclinical drug development studies are in vivo xenograft tumour models.

In a seventh aspect, the present invention provides a method for determining a prognosis of progression of a cancer in a subject, the method comprising the steps of:

(a) assessing a level of a first biomarker selected from at least one of Mcm2-7 in a biological sample from the subject; and (b) assessing the level of a second biomarker selected from at least one of geminin, Aurora A, Plk1, Ki67 and H3S10ph in the biological sample from the subject, wherein the combination of the level of the first biomarker compared to a pre-determined value and the level of the second biomarker compared to a pre-determined value is indicative of cancer progression in the subject.

In one embodiment, the method of determining the progression of cancer in the subject further comprises assessing the level of a third biomarker selected from at least one of geminin, Aurora A, Plk1, Ki67 and H3S10ph in the biological sample from the subject, wherein the second and third biomarkers are different.

In an eighth aspect, the present invention provides a method for determining a treatment protocol for a subject having cancer, the method comprising the steps of:

(a) assessing a level of a first biomarker selected from at least one of Mcm2-7 in the biological sample from the subject; and (b) assessing the level of a second biomarker selected from at least one of geminin, Aurora A, Plk1, Ki67 and H3S10ph in the biological sample from the subject, wherein the combination of the level of the first biomarker compared to a pre-determined value and the level of the second biomarker compared to a pre-determined value is indicative of the treatment regimen prescribed for the subject.

In one embodiment, the method of determining a treatment protocol for a subject having cancer further comprises assessing the level of a third biomarker selected from at least one of geminin, Aurora A, Plk1, Ki67 and H3S10ph in the biological sample from the subject, wherein the second and third biomarkers are different.

In a ninth aspect, the present invention provides a method for determining efficacy of a therapeutic treatment of a subject having cancer, the method comprising the steps of:

(a) assessing the level of a first biomarker selected from at least one of Mcm2-7 in the biological sample from the subject; and (b) assessing the level of a second biomarker selected from at least one of geminin, Aurora A, Plk1, Ki67 and H3S10ph in the biological sample the subject, wherein the combination of the level of the first biomarker compared to a pre-determined value and the level of the second biomarker compared to a pre-determined value is indicative of the efficacy of the therapeutic treatment.

BRIEF DESCRIPTION OF THE DRAWINGS

Further disclosure, objects, advantages and aspects of the present invention may be better understood by those skilled in the relevant art by reference to the following description of preferred embodiments taken in conjunction with the accompanying drawings, which are given by way of illustration only, and thus are not limiting to the scope of the present invention, and in which.

DETAILED DESCRIPTION

Figure 1:
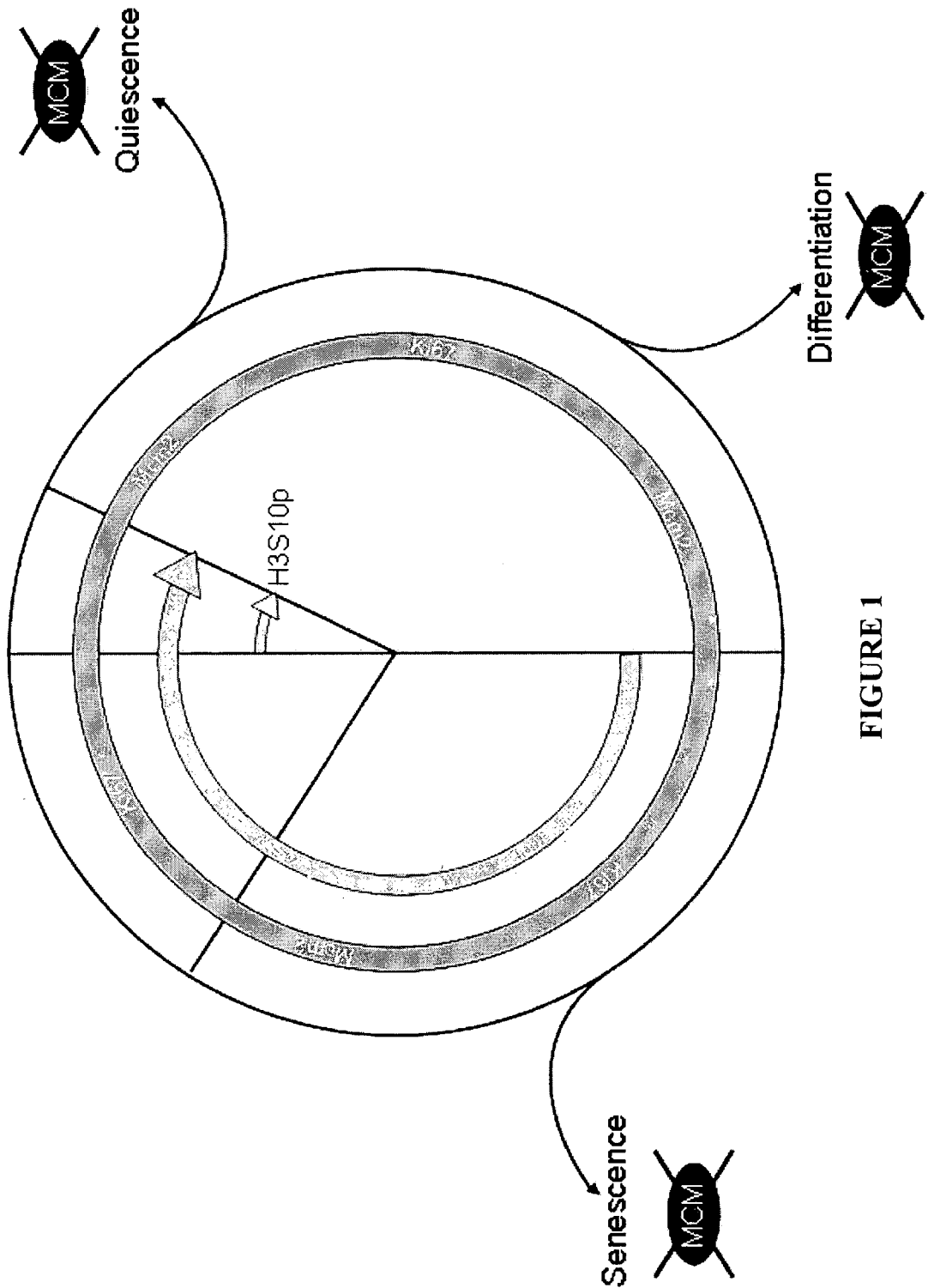
FIG. 1 shows the presence of Ki67, Mcm2, geminin, Aurora A and H3S10ph during the mitotic cell division cycle. Levels of the Mcm2-7 DNA replication licensing factors do not vary significantly during passage through the cell cycle, whereas expression of the endogenous licensing repressor protein geminin is restricted to S-G2-M phase. Increased geminin expression has been noted in several malignancies and correlates positively with proliferation. Notably, this increased expression is always restricted to S-G2-M, even in aggressive tumours. Aurora A (and PLK1; data not shown) levels are negligible during G1, and increase during S phase to reach a peak during G2/M. Presence of H3S10ph is restricted to mitosis and thus can be used as a mitotic marker. Mcm 2-7 protein expression can be used to determine cell cycle state in tissues. Mcm2-7 identify cells engaged in cell cycle (G1-S-G2-M phases) but are tightly down-regulated following withdrawal into quiescent (G0), differentiated, and senescent "out of cycle" states. Since Ki67 is expressed throughout the cell cycle in proliferating cells, the ratio of an S-G2-M phase or M phase marker with Ki67 (e.g. geminin/Ki67, Aurora A/Ki67 or H3S10ph/Ki67) can be used as an indicator of the relative length of G1 phase and therefore the rate of cell cycle progression.
Figure 2:
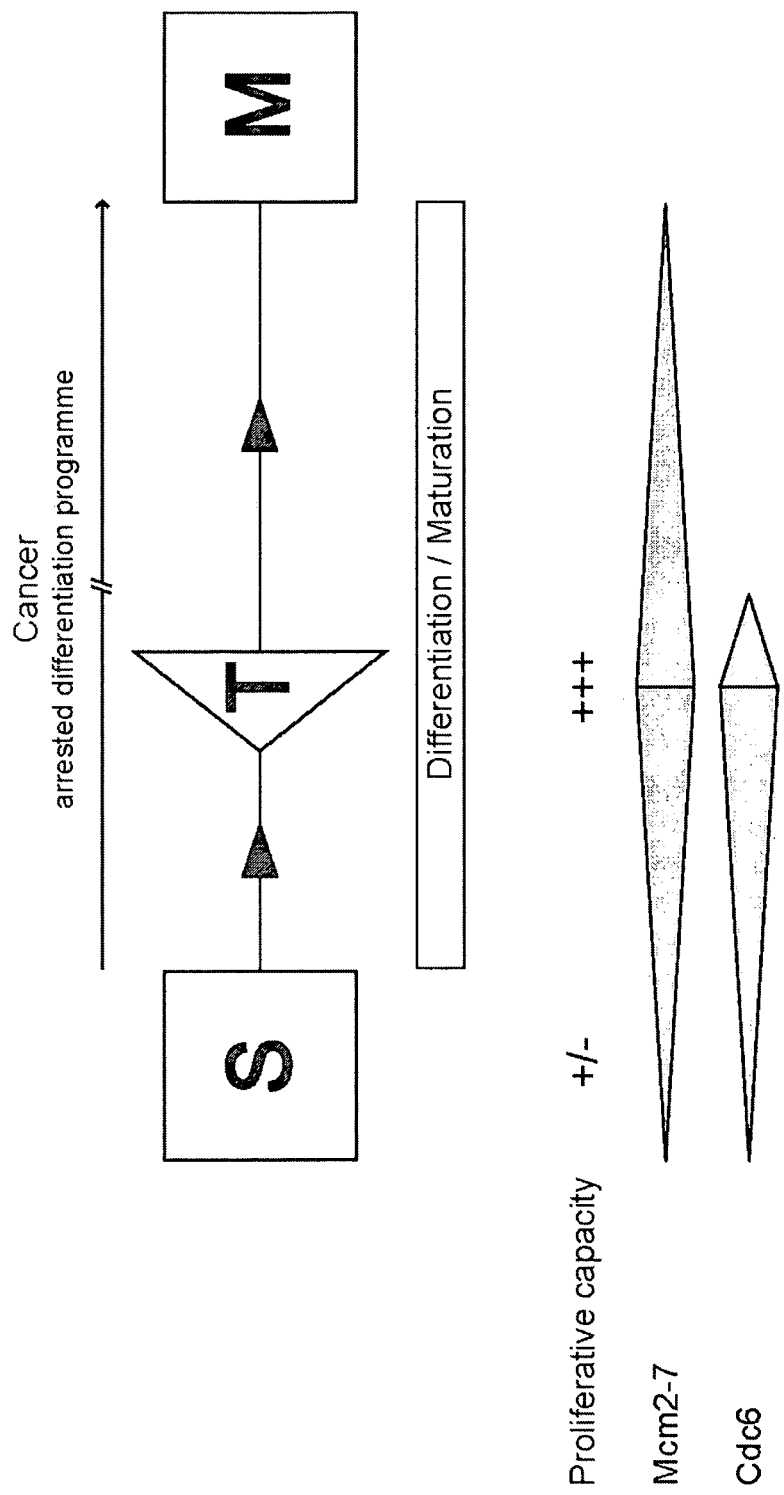
FIG. 2 shows a schematic diagram of DNA replication licensing factor expression in self-renewing tissues. The model includes stem cell, dividing-transit, and functional compartments. The flux of cells through these compartments is continuous; new cells are supplied from the stem cell compartment (S) and their number is amplified in the dividing-transit compartment (T). Cells become fully differentiated and functionally competent as they enter the mature compartment (M). The stem cell compartment shows low expression of the DNA replication licensing factors Mcm2-7. Mcm2-7 levels rapidly increase as cells enter the dividing-transit compartment. There is a gradual down-regulation of Mcm2-7 as cells differentiate and adopt a fully differentiated functional phenotype. However, proliferative capacity is lost at an earlier point during execution of the differentiation programme as cell exit the division-transit compartment and is coupled to down-regulation of the Mcm2-7 loading factor Cdc6. Notably, the arrested differentiation that characterizes cancer, particularly in high-grade tumours, is associated with a failure to down-regulate Mcm2-7.
Figure 3:
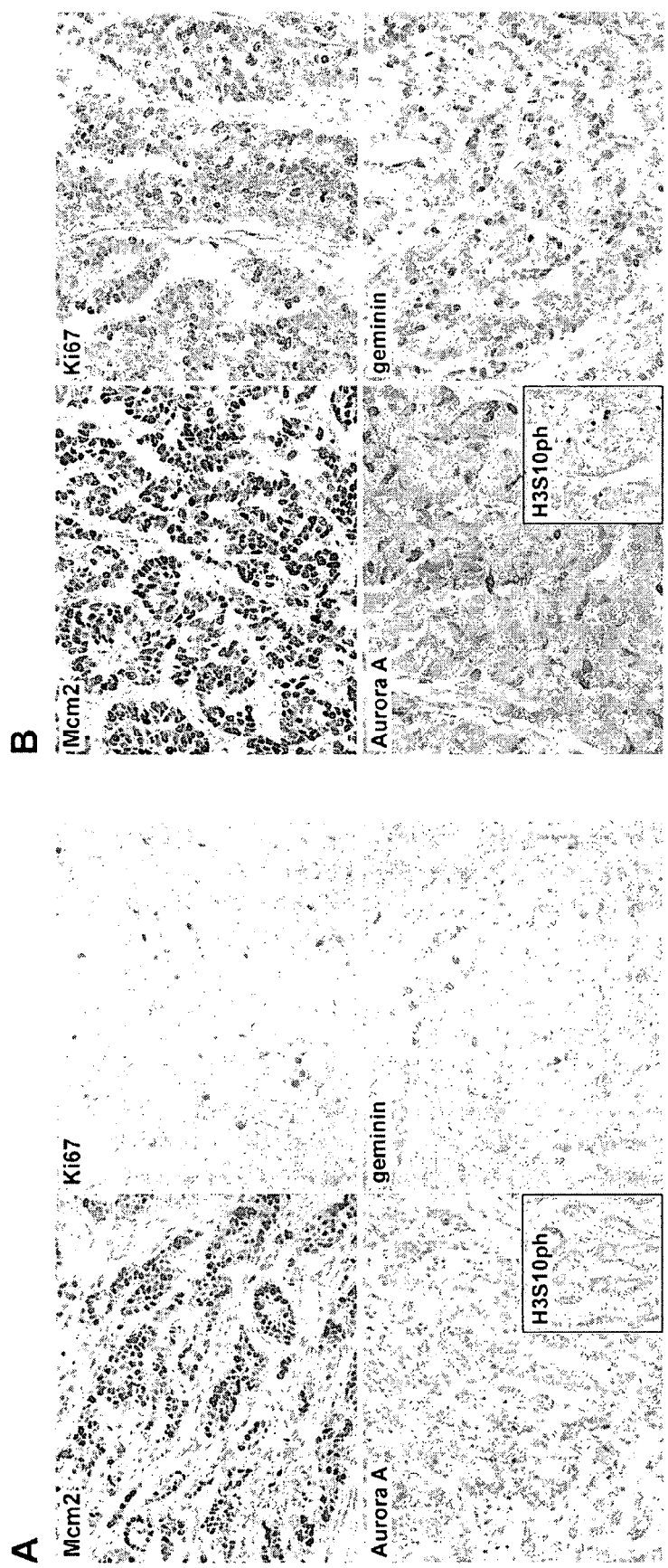
FIG. 3 shows cell cycle phase progression in breast cancer. Two breast cancer biopsy specimens immunostained for Mcm2, Ki67, geminin, Aurora A and H3p are shown and (A) and (B). Both cases are characterised by high Mcm2 protein expression, indicating that the majority of tumour cells are engaged in the cell division cycle. Although both tumour specimen show a high growth fraction as defined by Mcm2 expression, there are striking differences in expression of the S-G2-M markers geminin and Aurora A and the mitotic marker H3S10ph. (A) This tumour shows very low expression levels of geminin and Aurora A and a small number of cells show phosphorylation of Histone H3 at serine 10 (H3S10ph), indicating an arrested or prolonged G1 phase. (B) In contrast, this tumour shows high expression levels of geminin and Aurora A and increased H3S10 phosphorylation, indicating rapid cell cycle phase progression. Thus it can be postulated that the tumour shown in (B) is more responsive to S or G2/M cell cycle phase specific drugs.

The utility of biomarkers, including clinical utility, and how analysis of these biomarkers can be integrated with other key cell cycle regulators to provide information on cell cycle kinetics and phase distribution in patient tumour samples is provided. This analysis may provide diagnostic algorithms for improving prognostic assessment and also has potential to predict therapeutic response to cell cycle phase specific drugs. This is an approach in which a multiparameter cell cycle analysis may be performed on routine patient tumour biopsy material using biomarkers that form core constituents of the DNA replication licensing pathway and mitotic machinery. This algorithm provides not only a prognostic tool but can also be exploited as a predictive test for cell cycle phase specific drugs (including radiation) or drugs inhibiting upstream growth regulatory pathways. The algorithm can also be exploited to assess the efficacy of novel drug candidates in preclinical (in vivo xenograft tumour models) studies and clinical trials.

In a first aspect, the present invention provides a method of determining the presence or absence of abnormally proliferating cells or cellular growth abnormality in a body sample from an individual, the method including detecting in the sample a biomarker, wherein the biomarker is selected from group consisting of DNA replication licensing factors, Aurora kinases, Ki67, geminin, Polo-like kinases, and their substrate Histone H3 (referred to as "H3S10ph" hereinafter) and combinations thereof.

In one embodiment, the biomarker is detected using a specific binding member directed against a target polypeptide of the biomarker.

By "body sample" is intended any sampling of cells, tissues, or bodily fluids in which expression of a biomarker can be detected. Examples of such body samples include but are not limited to blood, lymph, urine, gynecological fluids, biopsies, and smears. Body samples may be obtained from a patient by a variety of techniques including, for example, by scraping or swabbing an area or by using a needle to aspirate bodily fluids. Methods for collecting various body samples are well known in the art. Body samples may be transferred to a glass slide for viewing under magnification. Fixative and staining solutions may be applied to the cells on the glass slide for preserving the specimen and for facilitating examination.

In one embodiment, the body sample is derived from any one of cervix, including testing cervical smears, the breast, urinary tract malignancies (tested on both biopsy tissue samples and on urine cytology smears), colon, lung, bladder, skin, larynx, oesophagus, bronchus, lymph nodes, and haematological malignancies, also blood and serum for evidence of metastatic sarcoma and carcinoma. In some embodiments, the present invention may additionally be employed in assessment of pre-malignant abnormalities of cervical glandular epithelial cells (glandular intra-epithelial neoplasia, GIN) or pre-malignant abnormalities in other tissues.

In some embodiments, it may be particularly appropriate for employment in cytological or biochemical assessment of other clinical specimens where detection of neoplastic cells, or their distinction from cells showing reactive changes, can be very difficult. Such specimens include sputum, bronchio-alveolar lavage specimens, urine and brushings from the alimentary tract (including oesophagus, stomach and pancreas, both bile duct and pancreatic duct).

In some embodiments, the present invention may be applied in histological or biological assessment of tissue where assessment of proliferation may enable more accurate prediction of clinical outcome, and/or more rational selection of therapy. Specimens may include malignancies of glandular cells (eg. lung, breast, colon, prostate, stomach), squamous cells (eg. lung, skin, oesophagus) or other epithelial cell types (eg. bladder, ureter, kidney, ovary).

In one embodiment, multiparameter analysis of Mcm2, Mcm3, Mcm4, Mcm5, Mcm6, Mcm7, geminin, Aurora A and Aurora B, and their substrate histone H3 may be used to evaluate the progression of EOC and the cell cycle kinetics of this tumour type, either in vitro or in vivo.

In a second aspect, the present invention provides a method of categorising a tissue as (i) normal or (ii) potentially or actually pre-cancerous or cancerous, dysplastic or neoplastic, the method including determining binding to a sample of the tissue of a specific binding member directed against a biomarker, wherein the biomarker is selected from group consisting of DNA replication licensing factors, Aurora kinases, Ki67, geminin, Polo-like kinases, H3S10ph and combinations thereof.

In one embodiment, the specific binding member is directed against a target polypeptide of the biomarker.

In one embodiment, the pattern or degree of binding may be compared with that for a known normal sample and/or a known abnormal sample.

In one embodiment, the ratio of one biomarker versus a further biomarker is determined.

A "biomarker" is any gene or protein whose level of expression in a biological sample is altered compared to that of a pre-determined level. The pre-determined level can be a level found in a biological sample from a normal or healthy subject. Biomarkers of the invention are selective for abnormally proliferating cells or cellular growth abnormality.

In another embodiment of the present invention, the biomarker is any gene or protein whose level is altered compared to a pre-determined level of expression in a biological sample. For example, the pre-determined value for a first biomarker in the biological sample is greater than 20%, greater than 25%, or 30% or greater of cells positive in the biological sample for the first biomarker.

In a related aspect, the pre-determined value for a second or third biomarker in the biological sample is less than 20%, less than 15%, less than 10% or 7% or less of cells positive in the biological sample for the second or third biomarker.

The biomarkers of the invention include genes and proteins, and variants and fragments thereof. Such biomarkers include DNA comprising the entire or partial sequence of the nucleic acid sequence encoding the biomarker, or the complement of such a sequence. The biomarker nucleic acids also include RNA comprising the entire or partial sequence of any of the nucleic acid sequences of interest. A biomarker protein is a protein encoded by or corresponding to a DNA biomarker of the invention. A biomarker protein comprises the entire or partial amino acid sequence of any of the biomarker proteins or polypeptides.

The present invention is based on the surprising discovery that targeting biomarkers of the DNA replication licensing pathway (eg Mcm2, Mcm3, Mcm4, Mcm5, Mcm6, Mcm7 and geminin) which regulates G1-S phase transition combined with biomarkers of the mitotic machinery (eg Aurora A and its substrate H3) which are involved in the G2-M transition, by immunoexpression profiling in routinely fixed surgical biopsy material, provides a unique insight into the cell cycle kinetics of these tumours. Using these combination of markers in a multiparameter analysis it is possible to determine whether tumour cells have withdrawn from cycle (i.e. sterile tumour cells), a population which will be resistant to cell cycle directed anti-cancer agents and radiation. Moreover for those tumour cells engaged in cycle (Mcm 2-7-positive) it is possible to determine the rate of cell cycle progression.

Tumours showing delayed progression and residing mainly in G1 are likely to show a poor response to S and G2-M phase directed agents (Table 1) and therefore should be treated with G1 directed agents (tumour phenotype—Mcm2-7 levels high but associated with low geminin, Aurora A and H3S10ph levels and geminin/Ki67 ratios tending towards zero). In contrast tumours showing accelerated cell cycle progression are likely to show a good response to S and G21M directed agents (Table 1) (tumour phenotype—Mcm2-7 levels high, geminin high, Aurora A high, H3S10ph high with geminin/Ki67 ratios tending towards 1). Tumours showing accelerated cell cycle progression and a high G2-M fraction are also likely to show the best response to radiation. Especially useful are binding molecules directed against core constituents of the DNA replication licensing pathway (Mcm2-7 family of proteins and geminin) and binding molecules directed against core constituents of the mitotic machinery (Aurora A, Polo-like kinase1 and H3S10ph). Other biomarkers may be utilized as a further parameter in the algorithm that allows analysis of the rate of cell cycle progression. Biomarkers that allow analysis of the rate of cell cycle progression include Ki67.

In one embodiment, the present invention provides a method of determining the cell cycle kinetics of tumour populations in routinely processed surgical biopsy material. The multiparameter algorithm allows non-proliferating out-of-cycle (sterile) cells that are refractory to cell cycle phase specific drugs and radiation to be distinguished from actively cycling cells. The multiparameter analysis allows the precise tumour cell cycle kinetics to be determined and thus allows the selection of cell cycle phase directed drugs most appropriate to treat that particular patient (personalised medicine) (Table 1). In addition to acting a potentially powerful predictive test for guiding therapeutic interventions, this multiparameter analysis provides a powerful prognostic tool for determining time to relapse (disease free survival/disease free interval) and time to death (overall survival).

In a third aspect, the present invention provides a method of marking abnormal cells within a tissue sample, the method including contacting the sample with a specific binding member directed against a target polypeptide, wherein the target polypeptide is selected from group consisting of DNA replication licensing factors, Aurora kinases, Ki67, geminin, Polo-like kinases, H3S10ph, and combinations thereof, under conditions wherein the specific binding member binds to abnormally proliferating cells and not normal cells.

Whether or not the specific binding member binds to the sample may be determined in order to ascertain the presence of abnormally proliferating cells within the sample.

In a fourth aspect, the present invention provides the use of a specific binding member directed against a target polypeptide, for determining, assessing or diagnosing the presence or absence of abnormal cellular proliferation, cellular growth abnormality, tumour cell cycle kinetics, cell cycle phase distribution, dysplasia, neoplasia, or a potentially or actually pre-cancerous or cancerous state in a tissue or sample thereof.

In one embodiment, the target polypeptide comprises two or more markers selected from the group comprising DNA replication licensing factors, Aurora kinases, Ki67, geminin, Polo-like kinases, H3S10ph and combinations thereof.

Precise duplication of DNA during each cell division cycle is essential for genomic stability and is achieved through tightly regulated initiation events. DNA replication initiation depends on the assembly of prereplicative complexes at replication origins during late mitosis and early $G_1$ phase. Prereplicative complex assembly involves sequential binding of origin recognition complex (ORC), Cdc6, Cdt1, and Mcm2-7 to origins and renders chromatin "licensed" for DNA synthesis during S phase. Regulation of DNA replication licensing factors such as Mcm2-7 protein levels, provides a powerful downstream mechanism for controlling cell proliferation in human tissues. Mcm2-7 dysregulation is an early event in multistep tumourigenesis. Inhibition of prereplicative complex reassembly, which ensures that origins are fired once-and-only-once per cell cycle, is critical for maintaining genomic integrity.

The licensing repressor geminin is expressed at high levels during S-G2-M phases and blocks Mcm2-7 reloading onto chromatin through its interaction with Cdt1. In human cell populations in vivo, depletion of geminin results in profound genomic instability with overreplication of DNA, resulting in the emergence of cells with giant aneuploid nuclei, which are the morphologic/pathologic hallmarks of aggressive cancers. Inactivation of geminin also causes centrosome overduplication, which, together with abrogated G2-M checkpoint mechanisms, results in multiple mitotic defects that may promote chromosome missegregation and aneuploidy. These findings emphasize the key role that geminin plays in maintaining genomic integrity at multiple stages of the cell cycle.

Rigorous control of mitotic events is essential for successful completion of sister-chromatid segregation and cell division. Although CDKs are the master regulators of mitotic entry, they do not act alone. Polo-like kinase 1 (PLK1), Aurora A and Aurora B are three additional protein kinases that control a subset of critical mitotic events. Transit through mitosis is dependent on protein kinases such as polo-like kinase (PLK) and the Aurora kinases. The Aurora kinases are important regulators of several stages of mitosis, including centrosome maturation and separation, chromosome orientation and segregation, and cytokinesis.

Like geminin, endogenous levels of the Aurora kinases are tightly regulated in a cell cycle-dependent manner, with low levels at G1-S, accumulation during G2-M, and rapid degradation at the end of mitosis.

Tumour cell cycle kinetics not only impacts on prognostic algorithms, but is also of importance for predicting response to cell cycle phase specific drugs (see above). Applicants have demonstrated that analysis of core constituents of the cell cycle machinery using simple immunohistological techniques, and applied directly to routine surgical biopsy material, provides a detailed and unique insight into the tumour cell cycle kinetic profile that is operating in vivo.

As discussed above, Mcm2, Mcm3, Mcm4, Mcm5, Mcm6 and Mcm7 (referred to herein as "Mcm2-7" or "Mcm2 to 7") expression allows cells traversing through the cycle to be distinguished from those residing in "out-of-cycle" states. The origin licensing inhibitor geminin is only detectable during S-G2-M phases, as are the mitotic kinases PLK1, Aurora A and B. Histone H3 is a substrate for the Aurora kinases and is phosphorylated only in mitosis. Phosphohistone H3 (H3S10ph) is thus a marker of M phase. Multi-parameter analysis of these G1/S and G2/M regulators therefore provides a detailed characterization of the cell cycle state in surgical biopsy material (routinely fixed and processed). For example, in resting premenopausal breast, Mcm2-7 expression is high but geminin, Aurora A/B, PLK1 and H3S10ph protein levels are low, indicating that mammary luminal epithelium resides in a G1 extended or arrested state, a phenotype also observed in premalignant lesions and slow growing neoplasms. In contrast, in rapidly growing aggressive tumours, not only are expression levels of Mcm2-7 high, but there is increasing expression of S-G2-M and M phase markers. This profile is indicative of accelerated cell cycle progression which appears to correlate with increasing tumour grade (less differentiated state), increasing genomic instability and reduced survival.

Cell cycle biomarker analysis is therefore of value as a predictor of therapeutic response, particularly for cell cycle phase specific drugs. For example, the expression levels of Aurora A and PLK1, potent targets for small molecule inhibitors, vary widely in ovarian and breast cancer. These tumours also display very different cell cycle kinetics and cell cycle phase distributions. Tumours showing accelerated cell cycle progression and high expression levels of these target proteins are most likely to show the greatest response to such mechanism based therapeutic interventions.

Analysis of cell cycle kinetics may also be used to monitor the response to drugs which impact on cell cycle progression through activation of checkpoint pathways in abnormally proliferating cells or cellular growth abnormality. For example, immunoexpression analysis of geminin, Aurora A, PLK1, H3S10ph and gemini/Ki67 in pre- and post-treatment biopsy material may provide a readout to identify tolerable doses of UCN-01 that can then be used to abrogate cisplatin-induced cell cycle arrest.

In some embodiments, immunocytochemistry techniques are provided that utilize antibodies to detect the overexpression of biomarker polypeptides in a sample from an individual. In this aspect of the invention, at least one antibody directed to a specific biomarker of interest is used. Overexpression can also be detected by nucleic acid-based techniques, including, for example, hybridization and RT-PCR. Kits comprising reagents for practicing the methods of the invention are further provided.

Although the methods of the invention require the detection of at least one biomarker in a patient sample for the detection of disease, in some embodiments 2, 3, 4, 5, 6, 7, 8, 9, 10 or more biomarkers may be used to practice the present invention. It is recognized that detection of more than one biomarker in a body sample may be used to identify instances of disease. Therefore, in some embodiments, two or more biomarkers are used, more preferably, two or more complementary biomarkers. By "complementary" is intended that detection of the combination of biomarkers in a body sample results in the successful identification of disease in a greater percentage of cases than would be identified if only one of the biomarkers was used. Thus, in some cases, a more accurate determination of disease can be made by using at least two biomarkers.

Accordingly, where at least two biomarkers are used, at least two antibodies directed to distinct biomarker polypeptides will be used to practice the immunocytochemistry methods disclosed herein. The antibodies may be contacted with the body sample simultaneously or concurrently.

In one embodiment, the method according to any one of the first to fifth aspect may comprise detecting in the sample a further target polypeptide, wherein the target polypeptide is selected from group consisting of cell cycle regulated genes that are specific to the G1/S phase boundary or to S-phase. Such genes include but are not limited to helicase (DDX11), uracil DNA glycolase (UNG), E2F5, cyclin E1 (CCNE1), cyclin E2 (CCNE2), CDC25A, CDC45L, CDC6, p21 WAF-1(CDKN1A), CDKN3, E2F1, NPAT, PCNA, stem loop BP (SLBP), BRCA1, BRCA2, CCNG2, CDKN2C, dihydrofolate reductase (DHFR), histone H1, histone H2A, histone H2B, histone H3, histone H4, MSH2, NASP, ribonucleotide reductase M1 (RRM1), ribonucleotide reductase M2 (RRM2), thymidine synthetase (TYMS), replication factor C4 (RFC4), RAD51, chromatin Factor 1A (CHAF1A), chromatin Factor 1B (CHAF1B), topisomerase III (TOP3A), ORC1, primase 2A (PRIM2A), CDC27, primase 1 (PRIM1), flap structure endonuclease (FEN1), fanconi anemia comp. grp A (FNACA), PKMYT1, and replication protein A2 (RPA2). Other S phase genes of interest include cyclin-dependent kinase 2 (CDK2), DNA polymerase I alpha (DNA POL1), DNA ligase 1, B-Myb, DNA methyl transferase (DNA MET), pericentrin (PER), KIF4, DP-1, ID-3, RAN binding protein (RANBP1), gap junction alpha 6 (GJA6), amino levulinate dehydratase (ALDH), histone 2A Z (H2A.Z), spermine synthase (SpmS), proliferin 2, T-lymphocyte activation protein, phospholipase A2 (PLA2), and L6 antigen (L6).

In some embodiments, the biomarkers comprise genes that are induced by the E2F transcription factor. Such genes include but are not limited to thymidylate synthase, thymidine kinase 1, ribonucleotide reductase M1, ribonucleotide reductase M2, CDK2, cyclin E, PCNA, DNA primase small subunit, topoisomerase II A (Topo2A), DNA ligase 1, flap endonuclease 1, RAD51, CDC2, cyclin A2, cyclin B1, cyclin B2, KIFC1, FIN16, BUB1, importin alpha-2, HMG2, enhancer of zeste, STK-1, histone stem-loop BP, Rb, P18-INK4C, annexin VIII, c-Myb, CDC25A, cyclin D3, cyclin E1, deoxycytosine kinase, DP-1, endothelin converting enzyme, enolase 2, P18 INK4C, ribonucleotide reductase, and uracil DNA glycolase 2. In particular embodiments the biomarker of interest is a gene induced by E2F transcription factor that is involved in cell cycle regulation and DNA replication, such as, for example, cyclin E2, p57KIP2, RANBPM, and replication protein A1. Some E2f-induced genes of interest are involved in apoptosis, including APAF1, Bcl-2, caspase 3, MAP3 Kinase 5, and TNF receptor associated factor. Other E2f-induced genes are involved in the regulation of transcription and include, for example, ash2 like, polyhomeotic 2, embryonic ectoderm protein, enhancer of zeste, hairy/enhancer of split, homeobox A10, homeobox A7, homeobox A9, homeodomain TF1, pre-B-cell leukemia FT3, YY1 TF, POU domain TF, TAFII130, TBP-factor 172, basic TF3, bromodomain/zinc finger, SWI/SNF, ID4, TEA-4, NFATC1, NFATC3, BT, CNC-1, MAF, MAFF, MAFG, core binding protein, E74-like factor 4, c-FOS, JUNB, zinc finger DNA BP, and Cbp/p300 transactivator. E2F-induced genes involved in signal transduction are also potential biomarkers of interest and include TGF beta, follistatin, bone morphogenetic protein 2, BMP receptor type 1A, frizzled homolog 1, WNT10B, sphingosine kinase 1, dual specificity phosphatase 7, dual specificity (Y) phosphatase, FGF Receptor 3, protein tyrosine phosphatase, dual specificity (Y) phosphatase D6655, insulin receptor, mature T-cell proliferation 1, FGF receptor 2, TGF alpha, CDC42 effector protein 3, Met, CD58, CD83, TACC1, and TEAD4.

If a tissue is categorised as potentially or actually pre-cancerous or cancerous, on the basis of detected abnormality in a tissue sample in accordance with the present invention, appropriate diagnostic and/or clinical follow-up will be called for.

The present invention also provides predictive methods for determining the course of therapy for the diagnosed condition.

Accordingly, in a fifth aspect, the present invention provides a method of predicting response to therapy or predicting disease progression in a cancer, the method comprising determining the presence or absence of abnormally proliferating cells or cellular growth abnormality in a body sample from an individual, the method including detecting in the sample a target polypeptide, wherein the target polypeptide is selected from group consisting of DNA replication licensing factors, Aurora kinases, Ki67, geminin, Polo-like kinases, H3S10ph and combinations thereof.

Cellular growth abnormalities include pre-cancerous or cancerous cells, other disorders of cellular proliferation including, but not limited to, psoriasis and inflammatory bowel disease such as ulcerative colitis and Crohn's disease.

In addition to being cellular proliferation disorders in their own right, inflammatory bowel diseases may be a precursor to a cancerous state, although not in all patients, so their detection by means of the present invention may be used to provide valuable results for closer follow-up. In inflammatory bowel disease there may be sloughing of cells of the colon and bowel, allowing for analysis to be performed on faecal samples and preparations of cells from such samples.

Samples to be subjected to a contact with a specific binding member in accordance with various aspects of the present invention may be prepared using any available technique which allows binding of a specific binding molecule to the target polypeptide, determination of nucleic acid levels, enzymatic activity and so on, in accordance with different embodiments of the present invention. Various techniques are standard in the art, e.g. (for molecules such as antibodies binding target polypeptide) as used in fixing cells for immunohistochemistry.

The detection of a specific binding member such as an antibody on control and test samples may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding binding molecule (e.g. antibody) and reporter molecule.

One favoured mode is by covalent linkage of each binding member with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed. Further examples are horseradish peroxidase and chemiluminescence.

A specific binding molecule may be provided in a kit, which may include instructions for use in accordance with the present invention. Such kits are provided as a further aspect of the present invention. One or more other reagents may be included, for example labelling molecules. Reagents may be provided within containers which protect them from the external environment, such as a sealed vial. A kit may include one or more articles for providing the test sample itself depending on the tissue of interest, e.g. a swab for removing cells from the buccal cavity, a syringe for removing a blood sample, a spatula for taking a cervical smear, a biopsy gun and so on (such components generally being sterile).

A kit may include any combination of or all of a blocking agent to decrease non-specific staining, a storage buffer for preserving binding molecule activity during storage, staining buffer and/or washing buffer to be used during antibody staining, a positive control, a negative control and so on. Positive and negative controls may be used to validate the activity and correct usage of reagents employed in accordance with the invention and which may be provided in a kit. Controls may include samples, such as tissue sections, cells fixed on coverslips and so on, known to be either positive or negative for the presence of the target, such as one or more of the biomarkers described herein. The design and use of controls is standard and well within the routine capabilities of those of ordinary skill in the art.

Samples may be removed from the body using any convenient means and technique. A spatula or swab may be used to remove endothelium cells, e.g. from the cervix or buccal cavity. Blood and other fluid samples may be removed using a syringe or needle. Other tissue samples may be removed by biopsy or tissue section.

In a sixth aspect, the present invention provides a method of monitoring response to therapy drug development studies, the method comprising detecting in a body sample a biomarker, wherein the biomarker is selected from group consisting of DNA replication licensing factors, Aurora kinases, Ki67, geminin, Polo-like kinases, and H3S10ph and combinations thereof, assessing the biomarker expression to determine the presence or absence of abnormal cellular proliferation, cellular growth abnormality, tumour cell cycle kinetics, cell cycle phase distribution, dysplasia, neoplasia, or a potentially or actually pre-cancerous or cancerous state in the sample.

In one embodiment, the drug development studies are pre-clinical drug development studies.

In one embodiment, the drug development studies are pre-clinical drug development studies.

In some embodiments, the preclinical drug development studies are in vivo xenograft tumour models.

A seventh aspect of the present invention provides a method for determining a prognosis of progression of a cancer in a subject, the method comprising the steps of:

(a) assessing a level of a first biomarker selected from at least one of Mcm2-7 in a biological sample from the subject; and (b) assessing the level of a second biomarker selected from at least one of geminin, Aurora A, Plk1, Ki67 and H3S10 ph in the biological sample from the subject, wherein the combination of the level of the first biomarker compared to a pre-determined value and the level of the second biomarker compared to a pre-determined value is indicative of cancer progression in the subject.

In a related embodiment, the method of determining the prognosis of progression of a cancer further comprises assessing the level of a third biomarker selected from at least one of geminin, Aurora A, Plk1, Ki67 and H3S10ph in the biological sample from the subject, wherein the second and third biomarkers are different.

In a further embodiment, when the level of the first biomarker compared to a pre-determined value is low and the level of the second biomarker compared to a pre-determined value is low, the subject's prognosis is indicative of a reduced likelihood of cancer progression.

In a related embodiment, when the level of the first biomarker compared to a pre-determined value is low and the level of the second biomarker compared to a pre-determined value is low, the subject's prognosis is indicative of a 5 year survival rate of greater than 80%, 85% or 89%.

In another embodiment, when the level of the first biomarker compared to a pre-determined value is high and the level of the second biomarker compared to a pre-determined value is low, the subject's prognosis is indicative of a reduced likelihood of cancer progression.

In a related embodiment, when the level of the first biomarker compared to a pre-determined value is high and the level of the second biomarker compared to a pre-determined value is low, the subject's prognosis is indicative of a 5 year survival rate of greater than 80%, 85% or 87%.

In a further embodiment, when the level of the first biomarker compared to a pre-determined value is high and the level of the second biomarker compared to a pre-determined value is high, the subject's prognosis is indicative of an increased likelihood of cancer progression.

In a related embodiment, when the level of the first biomarker compared to a pre-determined value is high and the level of the second biomarker compared to a pre-determined value is high, the subject's prognosis is indicative of a 5 year survival rate of less than 70%, 60% or 56%.

The levels of the biomarkers of the present invention can be measured using any means known to the skilled artisan. In one aspect, the levels of biomarkers can be measured using an immunological assay method, such as, but not limited to, dot blots, slot blots, RIA, microarray and ELISA. In another aspect, the levels of the biomarkers can be measured using a molecular biological-based assay method, such as, without being limited to, Northern blot analysis, Southern blot analysis, Western blot analysis, RT-PCR, PCR, nucleic acid sequence based amplification assays (NASBA), transcription mediated amplification (TMA), or computerized detection matrix.

It is important to note that the order in which the levels of the first, second, third or subsequent biomarkers are measured is not important. For example, all biomarkers may be measured concurrently. Alternatively, the second or third or subsequent biomarker may be assessed prior to the level of the first biomarker.

In an eighth aspect, the present invention provides a method for determining a treatment protocol for a subject having cancer, the method comprising the steps of:

(a) assessing a level of a first biomarker selected from at least one of Mcm2 to 7 in the biological sample from the subject; and (b) assessing the level of a second biomarker selected from at least one of geminin, Aurora A, Plk1, Ki67 and H3S10ph in the biological sample from the subject, wherein the combination of the level of the first biomarker compared to a pre-determined value and the level of the second biomarker compared to a pre-determined value is indicative of the treatment regimen prescribed for the subject.

In a related aspect, the method of determining a treatment protocol for a subject further comprises assessing the level of a third biomarker selected from at least one of geminin, Aurora A, Plk1, Ki67 and H3S10ph in the biological sample from said subject, wherein the second and third biomarkers are different.

In a further embodiment, when the level of the first biomarker compared to a pre-determined value is low and the level of the second biomarker compared to a pre-determined value is low, the treatment regimen is selected from one or more of:

(a) monitoring; and (b) treatment with non-cell-cycle specific chemotherapeutic agents.

In another embodiment, when the level of the first biomarker compared to a pre-determined value is high and the level of the second biomarker compared to a pre-determined value is low, the treatment regimen is selected from one or more of:
(a) monitoring;
(b) treatment with G1 or non-cell cycle specific agents; and
(c) treatment with non-S and G2/M cell cycle specific chemotherapeutic agents.

In yet a further embodiment, when the level of the first biomarker compared to a pre-determined value is high and the level of the second biomarker compared to a pre-determined value is high, the treatment regimen is selected from one or more of:
(a) surgery; and
(b) treatment with S and G2/M cell cycle specific chemotherapeutic agents.

Non-cell cycle chemotherapeutic agents include, without being limited to, mitomycin C (MMC), 1-(4-amino-2-methylpyrimidine-5-yl)-methyl-3-(2-chloroethyl)3-nitrosoure a hydro-chloride (ACNU), and nitrogen mustard (HN2), cisplatinum, 4-hydroperoxy-cyclo-phosphamide, Flavopiridol.

S-phase ell cycle agents include, without being limited to, 5-fluorouracil, hydroxyurea, methotrexate, epirubicin, etoposide, methotrexate, 5-fluororacil, 5-fluorodeoxyuridine, cytarabine, gemcitabine, cladribine, thioguanine, fludarabine, Hydroxyurea, topoisomerase I inhibitors (irinotecan, topotecan), Topoisomerase II inhibitors (etoposide, teniposide, anathracyclines, epirubicin).

G1 cell cycle agents include, without being limited to, asparaginase, prednisolone.

G2/M cell cycle agents include, without being limited to, etoposide, cisplatin, staurosporine, ZM447439, Vinca alkaloids, (vindesine, vinelobrine, vincristine, vinblastine), Taxanes (paclitaxel, docetaxel), Bleomycin, staurosporine, ZM447439 (Aurora kinase A and B inhibitor), BI2536 (Polo-like kinase I inhibitor).

M cell cycle agents include, without being limited to, docetaxel, BI 2536.

Agents which work at multiple steps within a cell cycle include, without being limited to, Flavopiridol.

While this invention has been described in connection with specific embodiments thereof, it will be understood that it is capable of further modification(s). This application is intended to cover any variations, uses or adaptations of the invention following in general, the principles of the invention and comprising such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the present invention as defined in the appended claims. Various modifications and equivalent arrangements are intended to be included within the spirit and scope of the present invention and appended claims.

"Comprises/comprising" when used in this specification is taken to specify the presence of stated features, integers, steps or components but does not preclude the presence or addition of one or more other features, integers, steps, components or groups thereof."

EXAMPLES

Example 1

DNA Replication Licensing Factors and Mitotic Kinases Define Proliferative State and are Linked to Clinical Outcome in Breast Cancer Study Cohort 182 patients diagnosed with invasive breast cancer were identified from the breast cancer database held in the department of Surgery, UCL Hospitals, London, UK. All patients studied underwent regular postoperative clinical assessment and contributed to the cross-sectional analyses. 10 were lost to follow-up and 5 had recurrent cancer, of whom 2 died from breast cancer. 167 patients contributed to the prospective analyses of survival and relapse, of whom 24 (14%) died from cancer within the study period, 12 died from other unrelated causes, and 131 were still alive at last follow-up. There were 40 (24%) relapse events comprising relapses and deaths from cancer. The median follow-up period was 47 months (range: 1-92 months). The mean time to relapse amongst those who relapsed was 26 months (standard deviation (SD)=15 months, range: 2-55 months). The mean follow-up time amongst those who had not yet relapsed was 52 months (SD=20 months, range: 2-92 months). The mean survival time amongst those who had died was 21 months (SD=12 months, range: 4-44 months). The mean follow-up time amongst those who had not yet died was 50 months (SD=21 months, range: 1-92 months). Formalin-fixed, paraffin-embedded surgical breast tissue from these patients was retrieved from the pathology archives which included all three histological grades (1-3) as determined by the Nottingham modification of the Bloom and Richardson method. Histological reports and slides were available for all cases. These included 142 invasive ductal carcinomas, 26 lobular, four mucinous, one micropapillary and nine of mixed type. Parameters recorded included histological grade, tumour size, tumour type, lymph node status, lymphovascular invasion (LVI), age and NPI. We also studied randomly selected cases of normal breast tissue from 21 premenopausal women who had undergone reduction mammoplasty. Local research ethics committee approval for the study was obtained from the joint UCL/UCLH Committees on the Ethics of Human Research.

Antibodies

Rabbit polyclonal antibody against human geminin was generated as described (Wharton S B, Hibberd S, Eward K L, et al. Br J Cancer 2004; 91:262-9). Ki67 MAb (clone MIB-1) was obtained from DAKO (Glostrup, Denmark), Mcm2 MAb (clone 46) from BD Transduction Laboratories (Lexington, Ky.), oestrogen receptor-α (ER) MAb (clone 1D5) and progesterone receptor MAb (clone PgR 636) from DAKO, Aurora A MAb NCL-L-AK2 (clone JLM28) from Novocastra Laboratories (Newcastle, UK), Polo-like kinase 1 (PLK1) MAb (clone 35-206) and Histone H3 phosphorylated on Serine 10 (H3S10ph) PAb from Upstate (Lake Placid, N.Y.).

Cell Culture

Human MCF-7 breast epithelial adenocarcinoma cells (ATCC HTB-22) were cultured in EMEM (Gibco-BRL, Invitrogen, Carlsbad, Calif., USA) supplemented with 2 mM Glutamine, 1% Non-Essential Amino Acids, 10% FCS, 100 U/ml penicillin and 0.1 mg/ml streptomycin.

Preparation of Protein Extracts and Immunoblotting

MCF7 cells were harvested by treatment with trypsin, washed in PBS, and resuspended in lysis buffer (50 mM Tris-Cl pH 7.5, 150 mM NaCl, 20 mM EDTA, 0.5% NP40) at $2 \times 10^7$ cells/ml. After incubation on ice for 30 min, the lysate was clarified by centrifugation (13,000 g, 15 min, 4° C.). Lysates were separated by 4-20% SDS-PAGE [75 µg protein/well] and immunoblotted as described (Stoeber et al. J Cell Sci, 114:2027-41, 2001). Blocking, antibody incubations, and washing steps were performed using the following conditions: PBS/0.1% Tween-20/5% milk for Mcm2, Aurora A and PLK1, PBS/1% Tween-20/10% milk for geminin, and PBS/5% milk for H3S10ph.

Immunohistochemistry

Archival formalin-fixed, paraffin-embedded tissue (PWET) obtained at initial diagnosis was available for all patients and for each specimen a block was chosen that contained a representative sample of invasive tumour. 3 µm sections were cut onto Superfrost Plus slides (Visions Biosystems, UK), dewaxed in xylene, and rehydrated through graded alcohol to water. Tissue sections were pressure cooked in 0.1 M citrate buffer at pH 6.0 for 2 min and immunostained using the Bond™ Polymer Refine Detection kit and Bond™-Max automated system (Vision Biosystems, Newcastle Upon Tyne, UK). Primary antibodies were applied at the following dilutions: Ki67 (1/300), Mcm2 (1/2000), geminin (1/600), ER (1/200), PR (1/200), Aurora A (1/70), PLK1 (1/1000) and H3S10ph (1/300). HER-2 immunostaining was performed using the DAKO HercepTest™ (DAKO), according to the manufacturer's instructions. Coverslips were applied with Pertex mounting medium (Cell Path Ltd, Newtown Powys, UK). Incubation without primary antibody was used as negative control and colonic epithelial sections as positive controls.

Protein Expression Profile Analysis

Protein expression analysis was performed by determining the labelling index (LI) of the markers in each tumour as described (Shetty at al. Br J Cancer 93:1295-300, 2005, Dudderidge et al. Clin Cancer Res 11:2510-7, 2005). Slides were evaluated at low power magnification (100×) to identify regions of tumour with the highest intensity of staining. From these selected areas, three to five fields at 400× magnification were captured with a charged coupled device camera and analysis software (SIS, Münster, Germany). Images were subsequently printed for quantitative analysis, which was undertaken with the observer unaware of the clinico-pathological variables. Both positive and negative cells within the field were counted and any stromal or inflammatory cells were excluded. Criteria for identification of positive cells were dependent on the biomarker: for Ki67, Mcm2, geminin, ER, PR and H3S10ph, cells with any degree of nuclear staining were scored positive; for Aurora A and PLK1, cells with any degree of nuclear or cytoplasmic staining were scored positive (Gritsko et al. Clin Cancer Res 9:1420-6, 2003). A minimum of 500 cells were counted for each case. The LI was calculated using the following formula: LI=number of positive cells/total number of cells×100. For evaluation of HER-2 protein over-expression, membrane staining was assessed following the FDA approved scoring system recommended by DAKO.

DNA Image Cytometry

For each case, one 40 µm section of PWET obtained from the same block as that assessed by IHC was used to prepare nuclei as described (Sudbo et al. N Engl J Med 344:1270-8, 2001. Haroske et al. Anal Cell Pathol 1998; 17:189-200, 1997). The Fairfield DNA Ploidy System (Fairfield Imaging Ltd, Nottingham, UK) was used for image processing, analysis and classification as described (Sudbo et al. 2001 supra.). Lymphocytes and plasma cells were included as internal controls and 40 µm sections of high-grade bladder tumour and normal colonic tissue as external controls for aneuploid and diploid populations, respectively. Histograms were classified according to published criteria (Sudbo et al. 2001 supra, Haroske 1998 supra). Histograms were classified by two independent assessors with a high level of agreement without knowledge of clinico-pathological variables. For statistical analysis, tetraploid and polyploid tumours were grouped together with aneuploid tumours.

Statistical Analysis

Biomarkers were summarised with the median and interquartile range. The Mann-Whitney U-test was used to compare each marker with Lymph node stage, ploidy status, and with grade 3 against the normal sample. The Jonckheere-Terpstra non-parametric test for trend was used to compare markers with grade and Her2 status. Spearman's rank correlation coefficient was used to assess associations between markers and NPI. The chi-squared test for linear by linear association with one degree of freedom was used to test for association between Her2 and ploidy status. The unpaired t-test was used to compare mean NPI according to ploidy status.

Linear regression was used to assess for trend in mean NPI across Her2. Cox regression was used in the analysis of cancer recurrence and cancer death to provide hazard ratios and to assess the prediction of markers, split into two categories at the median, both in univariate models and in multivariate models adjusting for NPI. Kaplan-Meier plots were used to show the estimated predictive effects of markers ignoring, and also stratified by, NPI category. All analyses involved two-sided tests, with effects summarised using 95% confidence intervals and assessed as statistically significant at the 5% level using SPSS software (version 12.0.1).

Results

Figure 5:
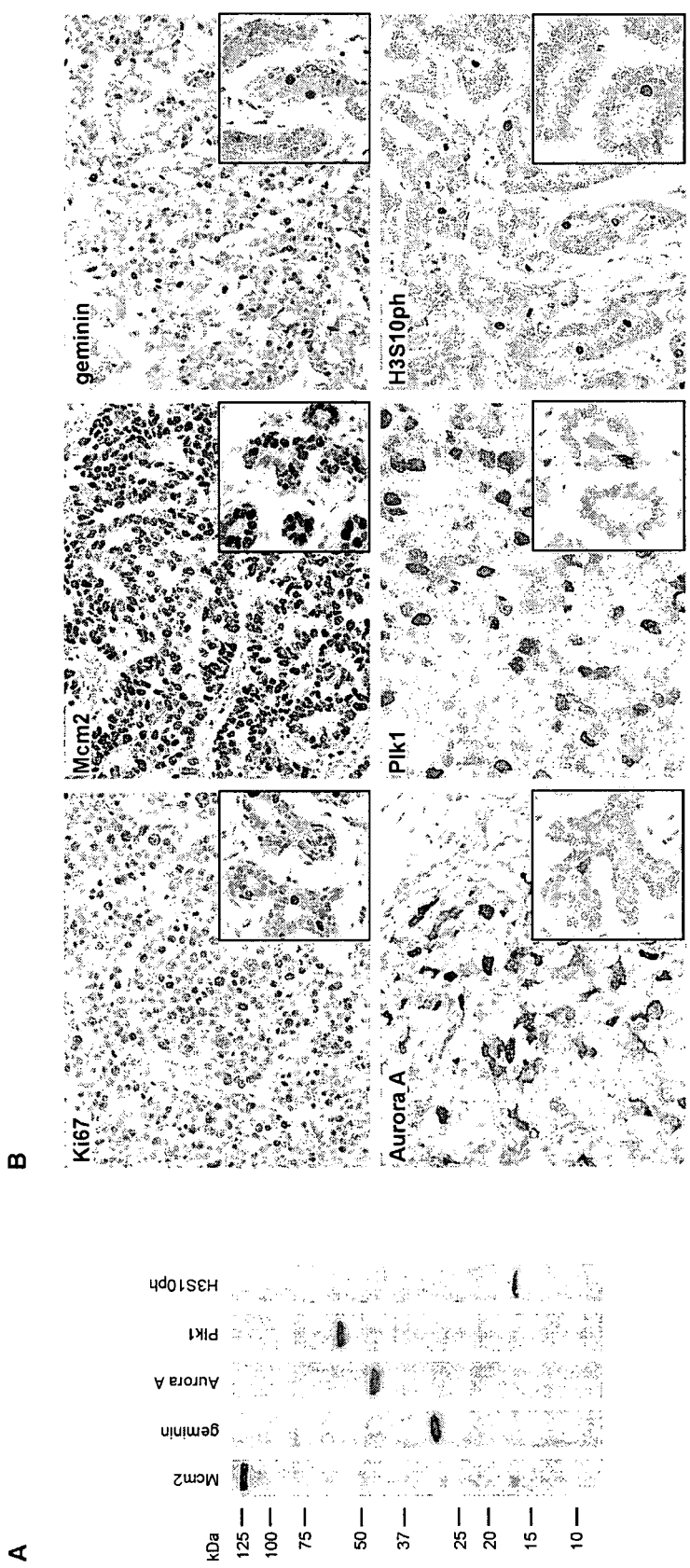
FIG. 5 shows a validation of the biomarker multi-parameter analysis. (A) Immunoblots of asynchronous MCF-7 total cell lysates with antibodies to Mcm2, geminin, Aurora A, Plk1 and H3S10ph. (B) Photomicrographs of paraffin-embedded tissue sections of Grade 3 breast cancer immunohistochemically stained with antibodies to Ki67, Mcm2, geminin, Aurora A, Plk1 and H3S10ph (Original magnification 400×). Inset shows immunostaining of normal breast (Magnification 800×).

Validation of Biomarker Multi-Parameter Analysis and its Biological Implications Monospecificity of antibodies against Mcm2, geminin, Aurora A, PLK1 and H3S10ph was confirmed in total cell extracts from asynchronous MCF7 cells by detection of a single protein with a molecular mass consistent with the reported electrophoretic mobility of the corresponding human antigen (FIG. 5A). In a separate study of this biomarker set in HeLa S3 cells and SK-OV 3 ovarian cancer cells we have demonstrated that Mcm2 levels do not vary significantly during passage through the cell cycle, whereas geminin expression is restricted to S-G2-M. Aurora A and PLK1 levels are negligible during G1, increase during S phase and reach a peak during G2/M, with degradation occurring 2-4 hours after release from mitotic arrest. Presence of H3S10ph is restricted to mitosis, consolidating the rational for its use as a mitotic marker. Since the proliferation marker Ki67 is present throughout the cell cycle in proliferating cells, the ratio of an S-G2-M phase or M phase marker with Ki67 (e.g. geminin/Ki67, Aurora A/Ki67 or H3S10ph/Ki67) can be used as an indicator of the relative length of G1 phase and therefore the rate of cell cycle progression. Notably, increased geminin expression is restricted to S-G2-M, even in aggressive tumours.

Protein expression analysis of these cell cycle markers was first studied in normal breast specimens following reduction mammoplasty (n=21). High level Mcm2 expression was observed in epithelial cells of the terminal duct lobular unit (TDLU), indicating that these cells reside in an "in-cycle" state (median: 33.5%). Whereas the level of Mcm2 expression was high, Ki67 was expressed at low levels (median: 2.8%). Notably, geminin, Aurora A, PLK1 (S-G2-M phase makers) and H3S10ph (M phase marker) are only expressed in a very small fraction of cells (<1%) of the TDLU, indicating a block to cell cycle progression. Taken together, this cell cycle phenotype is consistent with a G1 arrested state. By contrast, invasive breast cancer showed high levels of biomarker expression indicative of cell cycle progression (FIG. 5B). There was a marked increase in the protein expression levels of Ki67, Mcm2, geminin, Aurora A, PLK1 and H3S10ph when comparing normal with aggressive grade 3 tumours (median values: Mcm2 [33.5 v 92.3%, p<0.001], Ki67 [2.8 v 40.2%, p<0.001], geminin [0.98 v 17.4%, p<0.001], Aurora A [0 v 11.7%, p<0.001], PLK1 [0.37 v 14.2%, p<0.001] and H3S10ph [0 v 2.5%, p<0.001]). This increase was associated with a marked decrease in the Mcm2/Ki67 ratio (median values: 9.3 v 1.71%, p<0.001). The reduction in the Mcm2/Ki67 value reflects a switch from a licensed non-proliferating G1 arrested state to an actively proliferating state and is associated with the expression of S-G2-M markers indicative of cell cycle progression.

Figure 6:
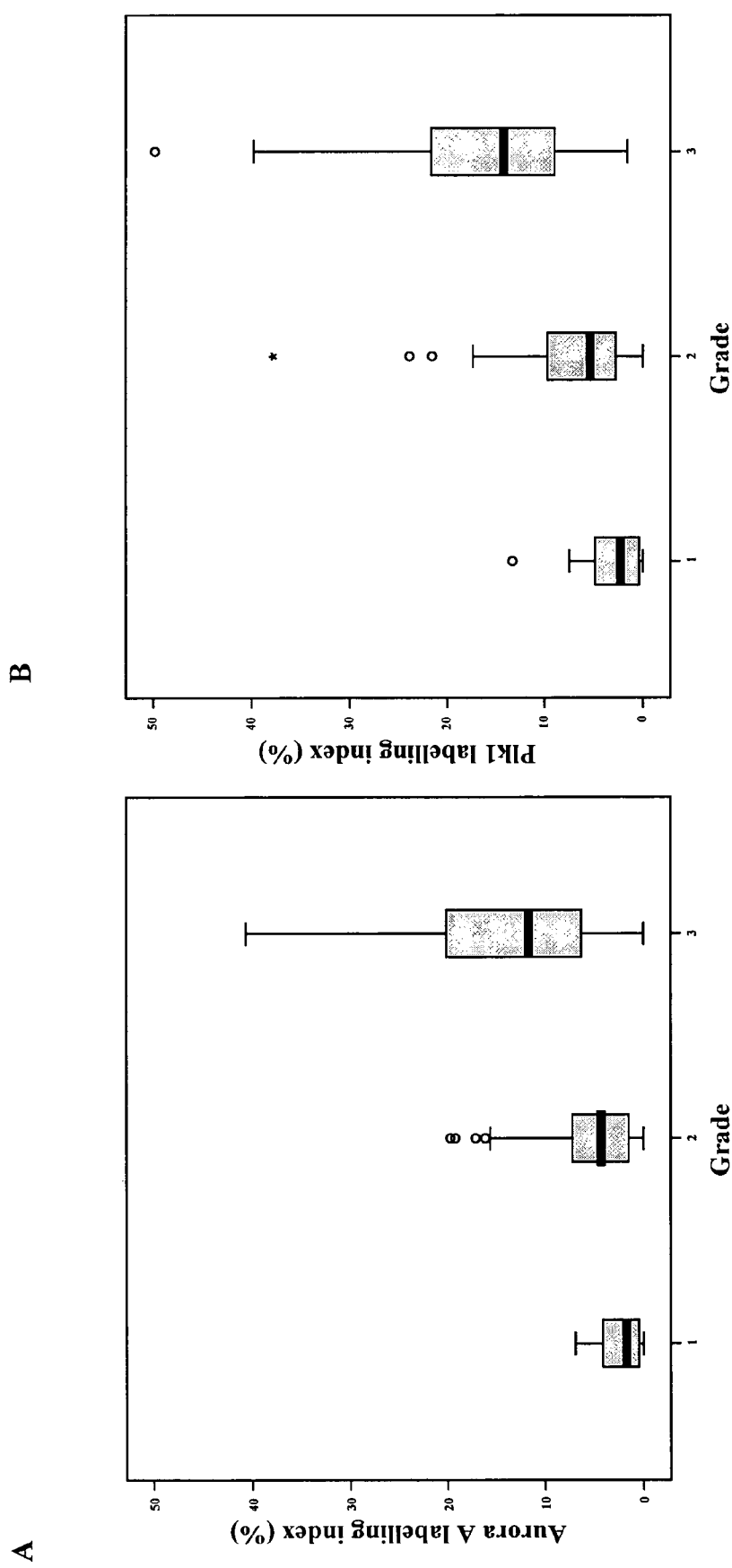
FIG. 6 shows Aurora A and Plk1 expression across tumour grades for breast cancer series.

Relationship Between Biomarkers, Tumour DNA Ploidy Status and Clinico-Pathological Parameters The clinico-pathological characteristics of the study are summarised in Table 2. Firstly, we examined the relationship between cell cycle biomarker expression and the differentiation status of the tumours. Expression levels of all six biomarkers were strongly associated with tumour grade (Table 3), however there is some overlap in the distribution of biomarker levels between the grades (e.g. Aurora A and PLK1 levels, FIG. 6). These data show an increasing proportion of cells engaged in cycle with increasing tumour anaplasia, but also indicate that the biomarkers do not fully distinguish between grades for all patients within each grade. In keeping with these findings, a highly significant association between tumour grade and ploidy status was found (p<0.001). The ratios geminin/Ki67, Aurora A/Ki67, Aurora B/Ki67 and H3S10ph/Ki67 showed no significant change with increasing grade, indicating that arrested differentiation was not associated with an accelerated rate of cell cycle progression in high-grade tumours (Table 3). This is in marked contrast with our findings in ovarian cancer in which accelerated cell cycle progression was observed with increasing tumour anaplasia (geminin/Ki67: p<0.007, Aurora A/Ki67: p<0.0002, H3S10ph/Ki67: p<0.0002). By contrast, and consistent with our findings in other tumour types, the Mcm2/Ki67 ratio decreased with increasing tumour grade, reflecting a shift in the proportion of DNA replication licensed but non-proliferating cells in well-differentiated tumours to actively cycling cells in poorly-differentiated tumours (Table 3). The positive correlation between geminin expression and increasing tumour anaplasia and genomic instability indicates that this origin licensing repressor does not appear to behave as a tumour suppressor in breast cancer. This has also been observed in other tumour types, for example in peripheral B-cell lymphomas and ovarian cancer, in which the number of geminin expressing cells is proportional to the cell proliferation index.

To investigate the relationship between the biomarkers and genomic instability, we linked their expression profiles to tumour DNA content (Table 4). There was a highly significant association between expression levels of all cell cycle biomarkers including Ki67 (p<0.001), Mcm2 (p=0.009), geminin (p<0.001), Aurora A (p<0.001), PLK1 (p=0.002) and H3S10ph (p<0.001) and genomic instability. There was also a significant decrease in the Mcm2/Ki67 ratio (p=0.004). Taken together, these data show an increased proportion of actively cycling cells in the aneuploid tumours compared to diploid tumours. Interestingly, again, as in the case of the differentiation status of these tumours, there was no evidence of accelerated cell cycle progression in aneuploid tumours and contrasting with our findings in ovarian cancer in which several cell cycle biomarker/Ki67 ratios increased.

No significant association was found between Ki67, Mcm2, geminin, Aurora A, PLK1 expression and lymph node metastasis (Table 5). A weak association with H3S10ph expression was observed (p=0.02). There was a strong inverse association with ER (p=0.007) and PR (p=0.005) expression. This contrast with our findings in ovary in which a significant association was found between Aurora A (p=0.006), H3S10ph (p=0.002), Aurora A/Ki67 (p=0.003), H3S10ph/Ki67 (p=0.005) and tumour stage, reflecting the role of Aurora A dysregulation in early epithelial ovarian tumourigenesis and progression to advanced stage disease. Expression levels of Ki67, Mcm2, geminin, Aurora A, PLK1, H3S10 ph showed a strong positive correlation, and ER and PR a negative correlation, with increasing NPI score (Table 6). There was also a significant decrease in the Mcm2/Ki67 ratio, signifying a switch from licensed non-proliferating state to actively proliferating state with increasing NPI score. Cell cycle biomarker expression was not significantly associated with Her2 status, but there was strong inverse association with PR expression (p<0.001) (Table 7). There was also an association between increasing NPI score and Her2 over-expression and a weak association was observed between aneuploidy and increasing NPI score (Table 8). A weak association was also observed between increasing Her2 score and aneuploidy (Chi-squared=3.03, p=0.082).

Relationship Between Biomarkers, Tumour DNA Ploidy Status and Patient Outcome

Univariate Analysis

Figure 7:
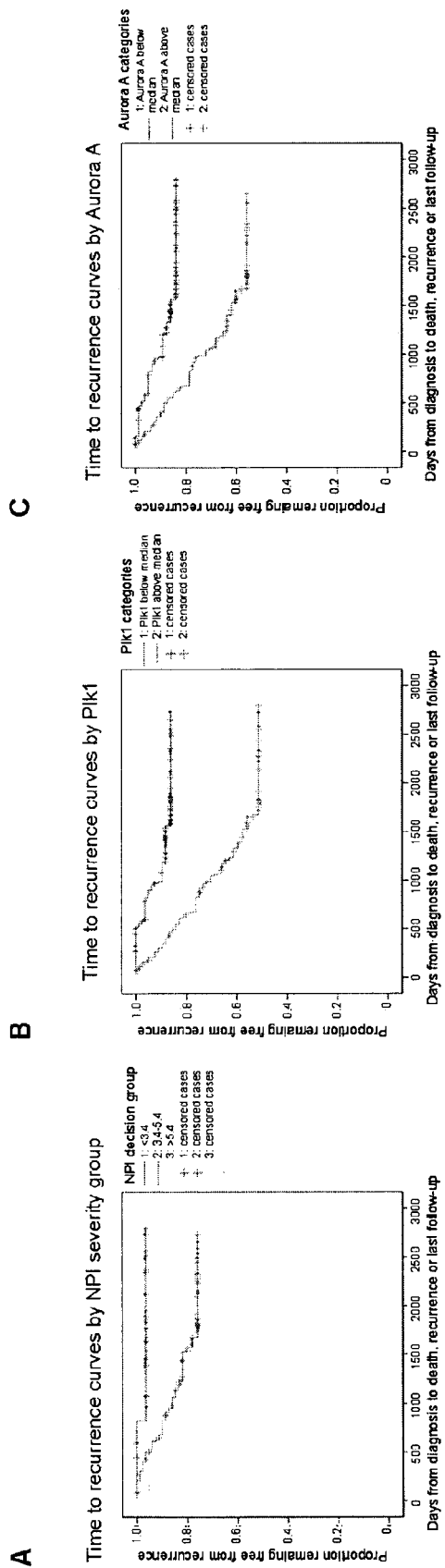
FIG. 7 shows time to recurrence curves by (A) NPI, (B) Plk1, and (C) Aurora A for breast cancer series.

The NPI score was a strong predictor of breast cancer recurrence and death in this patient cohort with the hazard of recurrence increasing just under two-fold per unit of NPI score (HR=1.81 [1.47-2.23], p<0.001) and the hazard of dying increasing just over twofold per unit of NPI score (HR=2.15 [1.61-2.88], p<0.001). Patient age was not a predictive factor (Table 9) (FIG. 7A). Ki67, Mcm2, geminin, Aurora A, PLK1, and H3S10 ph were identified as strong predictors of breast cancer recurrence (HR=2.77 [1.44-5.30], p=0.002; HR=3 [1.56-5.76], p<0.001; HR=3.93 [1.98-7.80], p<0.001; HR=3.31 [1.67-6.57], p<0.001; HR=4.48 [2.21-9.09], p<0.001; HR=3.49 [1.76-6.92], p<0.001 respectively) (FIGS. 7B and 7C). These associations were also observed for survival, but were not as strong due to smaller number of events in this cohort (Mcm2: HR=2.32 [0.99-5.43], p=0.05; geminin: HR=2.43 [1.04-5.68], p=0.04; Aurora A: HR=2.18 [0.93-5.12], p=0.07; PLK1: HR=3.46 [1.37-8.71], p=0.009; H3S10ph: HR=3.29 [1.31-8.30], p=0.01). A lower hazard of recurrence was observed in the diploid group, but this was not significant (HR=0.62 [0.33-1.18], p=0.14). There was a significant increasing trend in the hazard of recurrence and death through increasing categories of Her2 expression (HR=1.44 [1.13-1.83], p=0.003 and HR=1.40 [1.02-1.94], p=0.04, respectively).

Predictive Value of Biomarkers Over and Above NPI

Figure 8:
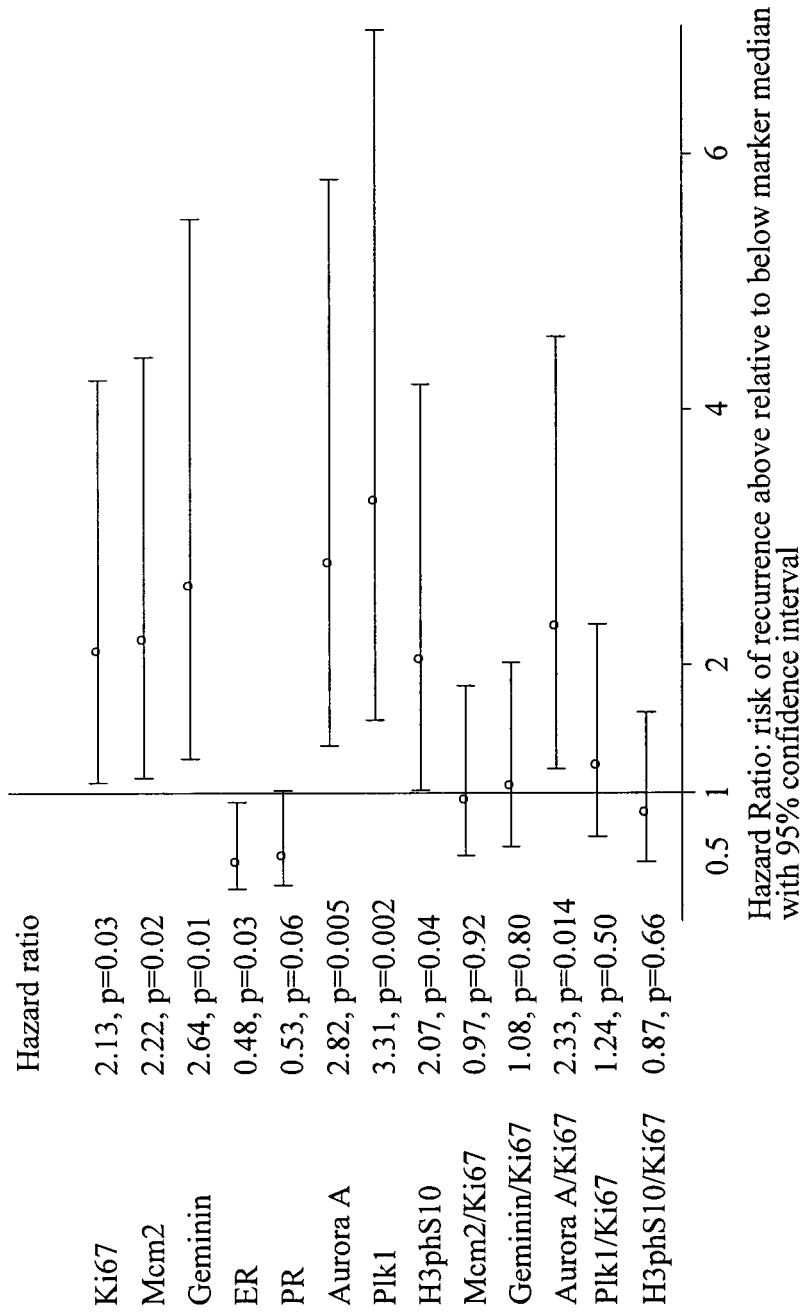
Figure 9:
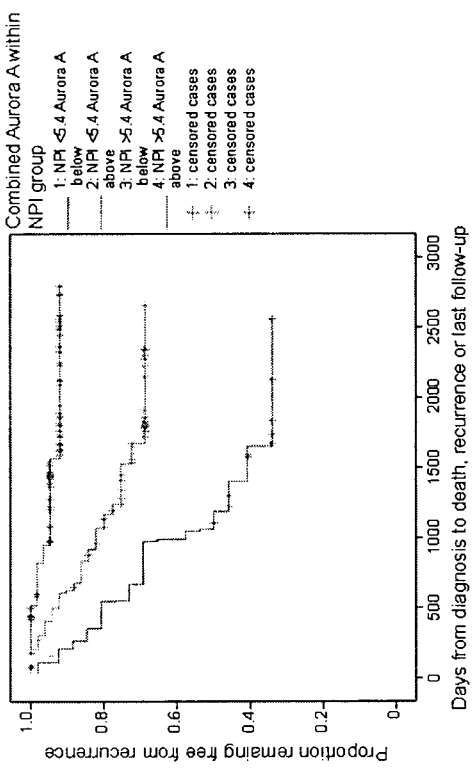
FIG. 9 shows time to recurrence curves by (A) NPI and Plk1 and (B) NPI and Aurora A for breast cancer series.
Figure 9:
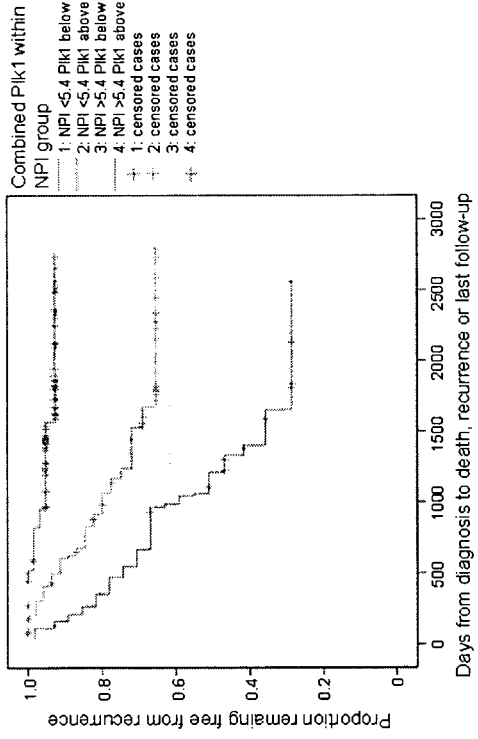

Multivariate analysis shows that the effects of these cell cycle biomarkers remain statistically significant and predictive of cancer recurrence even after adjusting for NPI. Ki67, Mcm2, geminin, Aurora A, PLK1, and H3S10ph were identified as strong independent predictors of breast cancer over and above NPI (HR=2.13 [1.08-4.23], p=0.03; HR=2.22 [1.12-4.41], p=0.02; HR=2.64 [1.27-5.49], p=0.01; HR=2.82 [1.37-5.80], p=0.005; HR=3.31 [1.57-6.97], p=0.002; HR=2.07 [1.02-4.20], p=0.04 respectively) (FIGS. 8 and 9). Although there was value in using one cell cycle biomarker to predict recurrence, no added value was achieved by including two or more markers. This is partly because there was correlation between markers and clinicopathological variables.

Interestingly the mitotic kinases, Aurora A and PLK1 were identified as the most powerful independent predictors of breast cancer recurrence.

Figure 4:
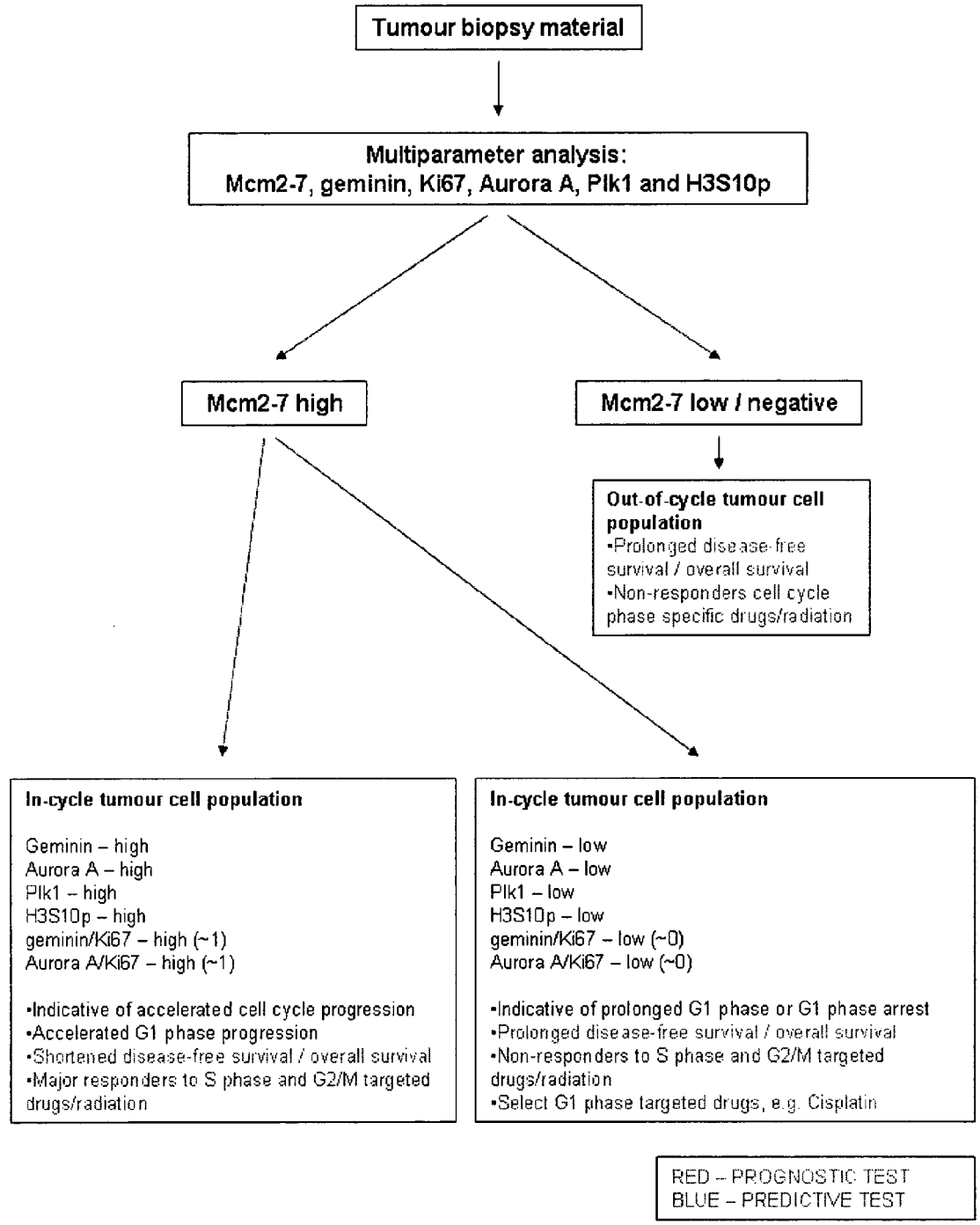
FIG. 4 shows multiparameter analysis of DNA replication licensing factors, Aurora kinases, Ki67, geminin, Polo-like kinases, H3S10ph and combinations thereof for prognostic and predictive cancer testing. Using these combination of markers in a multiparameter analysis it is possible to determine whether tumour cells have withdrawn from cycle (i.e. sterile tumour cells), a population which will be resistant to cell cycle directed anti-cancer agents and radiation. Moreover for those tumour cells engaged in cycle (Mcm 2-7-positive) it is possible to determine the rate of cell cycle progression.
Figure 13:
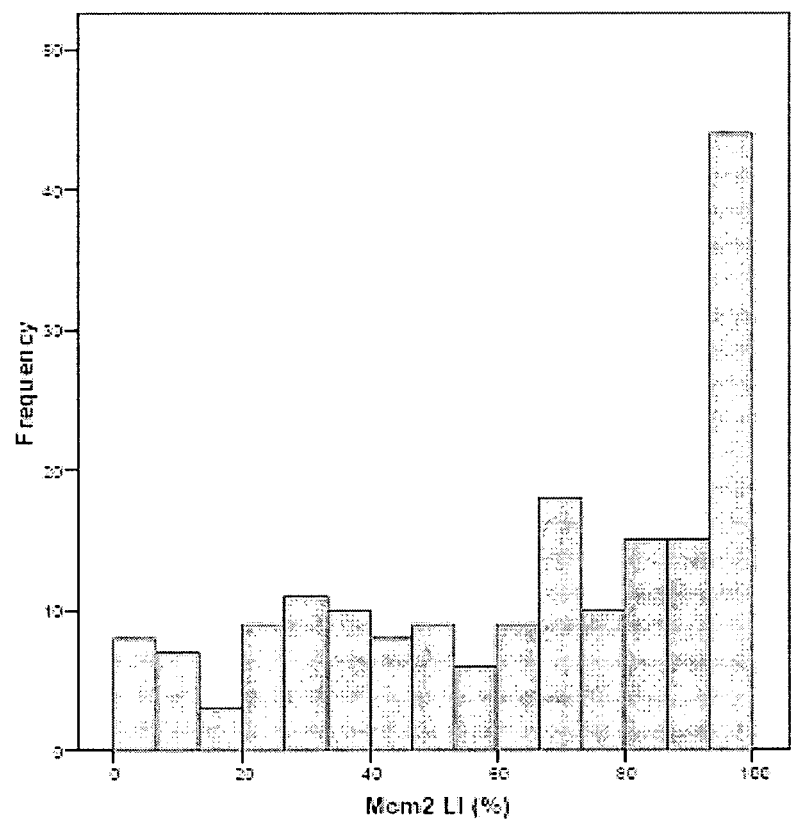
FIG. 13 is a graphical representation showing distribution of Mcm2 expression in the study sample. Frequency of Mcm2 protein expression across the breast cancer patient cohort. (Mean=64.4101, Std. Dev.=30.4632, N=182).
Figure 14:
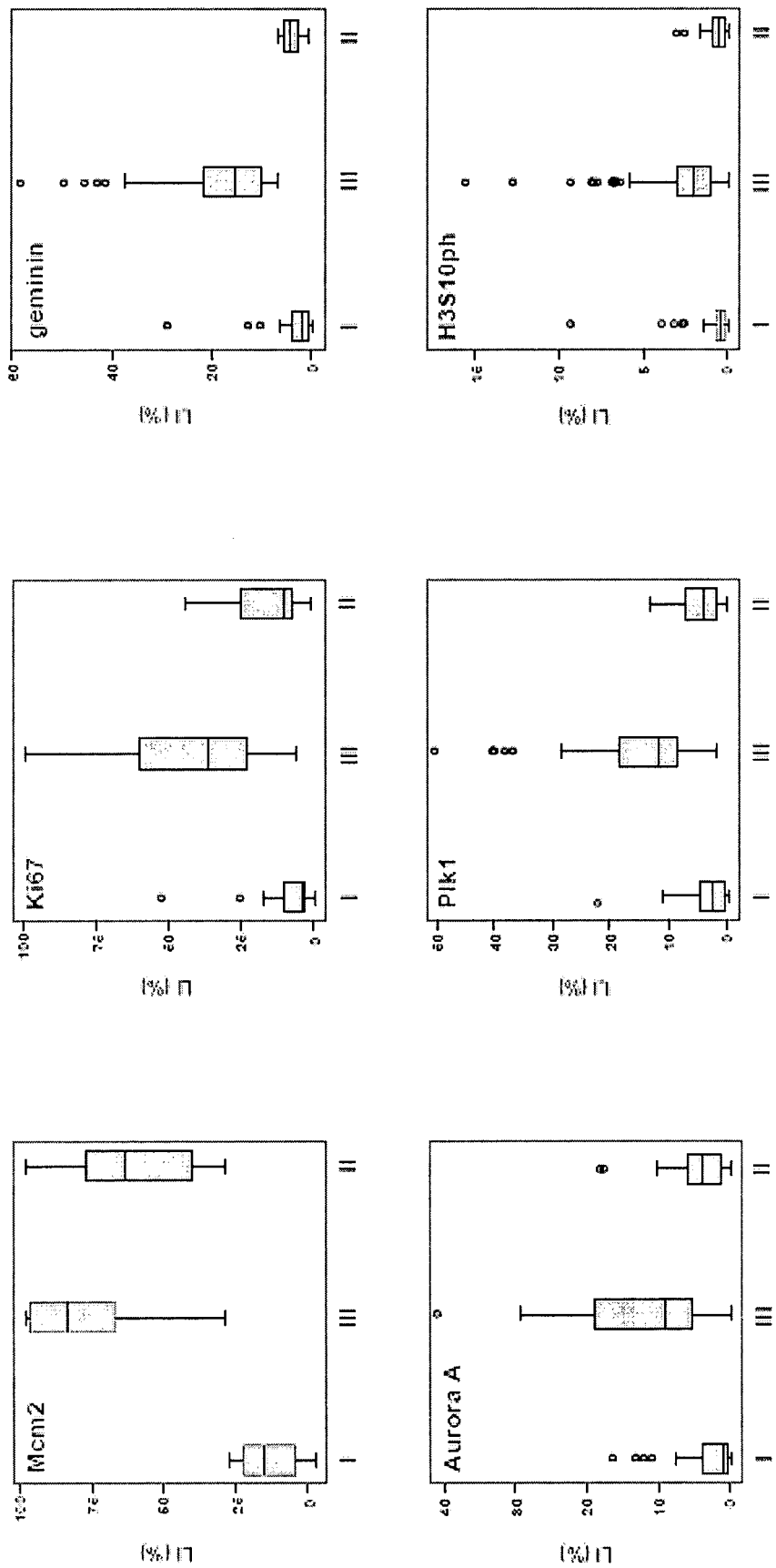
FIG. 14 is a graphical representation showing distribution of cell cycle biomarker expression defines three distinct cell cycle phenotypes; (I) out-of-cycle state; (II) in cycle G1 delayed/arrested state; (III) actively cycling state. The median (solid black line), interquartile range (boxed), and robust range excluding outlying cases (enclosed lines) are shown. Outlying cases are shown by isolated points. (LI: labeling index).

Relationship Between Cell Cycle Phenotype, Clinicopathological Variables and Patient Outcome We found that the individual cell cycle phase specific biomarkers are powerful independent prognostic markers in breast cancer. This raises the question whether the cell cycle kinetics or cell cycle phenotype of a tumour might also have an impact on the pathobiology of this particular tumour type. We have previously shown in our in-vitro DNA replication assays that downregulation of the Mcm2-7 licensing factors, constituents of the DNA helicase, is a ubiquitous downstream mechanism by which the proliferative capacity of cells is lowered as cells exit the cell division cycle into quiescent (G0), differentiated or senescent out of cycle states (Williams and Stoeber, Curr Opin Cell Biol 19:672-679, 2007; Blow and Hodgson, Trends Cell Biol 12:72-78, 2002; Stoeber et al., EMBO J 17:7219-7229, 1998; Stoeber et al., J Cell Sci 114:2027-2041, 2001; Kingsbury et al., Exp Cell Res 309:56-67, 2005; Barkley et al., Exp Cell Res 313:3789-3799, 2007). To determine the cell cycle phenotype, we selected a cut-point of 30% for Mcm2 protein expression to define a group (Mcm2<30%, phenotype I) in which the majority of tumour cells reside in an out-of-cycle state 9 FIG. 13, FIG. 14). This group (phenotype I), 18% of all tumours, had geminin levels of less than 7%. This is in keeping with our observations in in-vitro assays and self-renewing tissues that geminin is also tightly downregulated as cells enter quiescent (G0) and differentiated out-of-cycle states (Williams and Stoeber, 2007 supra; Eward et al., J Cell Sci 117:5875-5886, 2004; Kingsbury et al., 2005 supra; Barkley et al., 2007 supra) (FIG. 4, Table 1). In contrast, most cancers had Mcm2 expression levels above 30% (Mcm2>30%) in which a majority of tumour cells reside in an in-cycle state (Williams and Stoeber, 2007 supra) (FIG. 13, FIG. 14, Table 15). Fifty-eight percent of these tumours (phenotype III) displayed active cell cycle progression indicated by geminin levels above 7%, a cut point defined by the labelling index for the out-of-cycle state (FIG. 14, Table 15). Notably, a large number of breast cancers (phenotype II), 24% of all tumours, displayed an in-cycle phenotype (Mcm2>30%) but expressing geminin levels below 7% indicative of a G1 delayed or arrested state (Williams and Stoeber, 2007 supra; Stoeber et al., 2001 supra; Blow and Hodgson, 2002 supra; Shetty et al., Br J Cancer 93:1295-1300, 2005; Dudderidge et al., Clin Cancer Res 11:25110-2517, 2005; Gonzalez et al., J Pathol 204:121-130, 2004) (FIG. 14, Table 15). Importantly, the distribution of the other S-G2-M biomarkers between the three groups exactly mirrors that observed for geminin, further reinforcing segregation into three distinct cell cycle phenotypes (FIG. 14).

Figure 15:
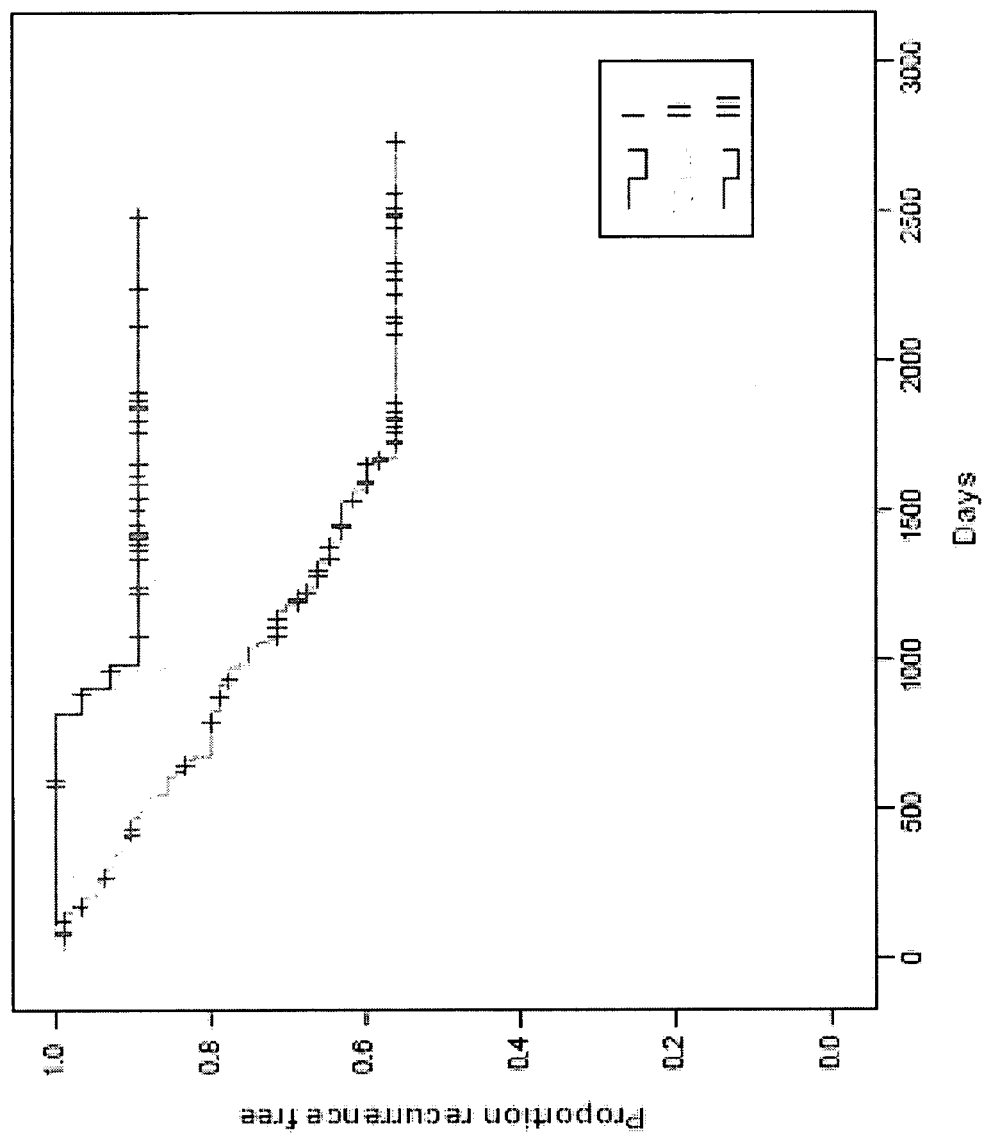
FIG. 15 is a graphical representation of Kaplan-Meier curves showing association between cell cycle phenotype and disease-free survival. (I) out-of-cycle state; (II) in cycle G1 delayed/arrested state; (III) actively cycling state. On univariate analysis comparing phenotype III with phenotypes I and II combined; HR=3.90 (1.81-8.40), p<0.001. On multivariate analysis adjusted for PI, HR=2.71 (1.18-6.23), p=0.19.
Figure 16:
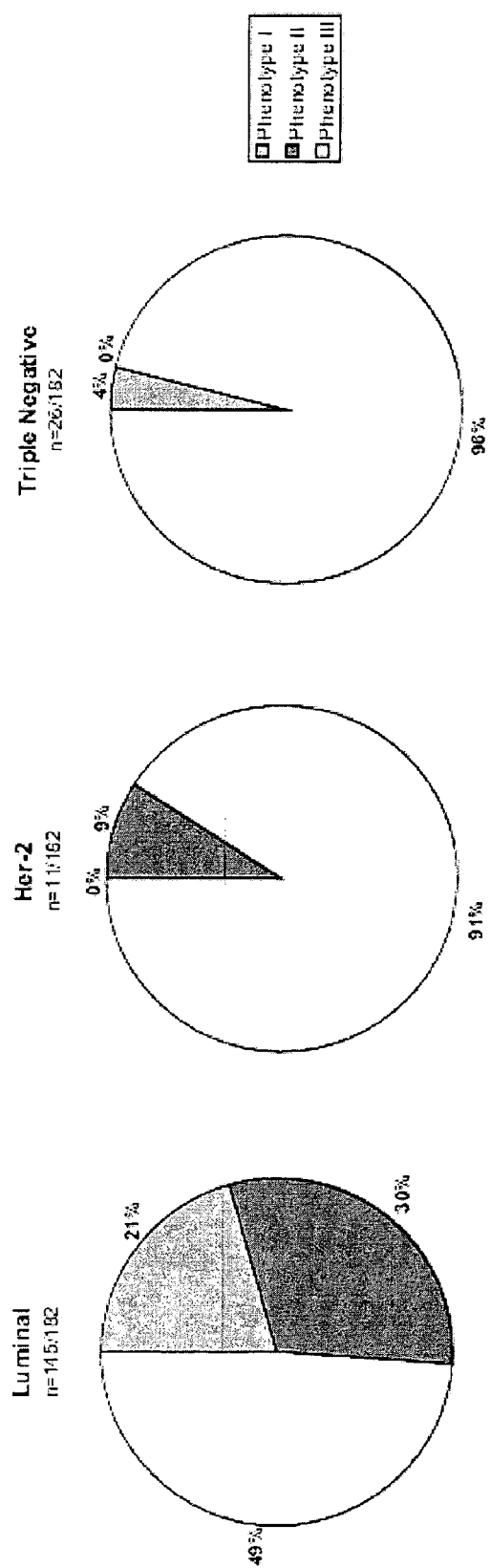
FIG. 16 is a graphical representation showing relationship between cell cycle phenotype and breast cancer subtypes. The panels shows the proportion of each breast cancer subtype which display cell cycle phenotypes I (out of cycle), II (G1 delayed/arrested) and III (actively cycling). Notably, the majority of Her-2 and triple negative tumours display the actively cycling phenotype (III).

Next, we investigated whether the cell cycle phenotype influences in-vivo behaviour and its association with clinicopathological variables including NPI. Notably, there was no association with age, tumour size, lymph node metastasis, ER/PR or Her-2 receptor status. However a greater proportion of grade 3 tumours, those exhibiting arrested differentiation, displayed the actively cycling phenotype. This cell cycle profile was also associated with a higher NPI score (p<0.001) (Table 15). Univariate and multivariate analysis adjusted for NPI also demonstrated that the cell cycle phenotype was a strong predictor of disease-free survival. The actively cycling phenotype (phenotype III) showed a much higher hazard of relapse than phenotypes I and II on both univariate and multivariate analysis, HR=3.90 (1.81-8.40), p<0.001 and HR=2.71 (1.81-6.23), p=0.019, respectively (FIG. 15). Intriguingly, an almost identical low hazard of relapse was observed between well differentiated out-of-cycle tumours and high grade tumours exhibiting a G1 delayed/arrested phenotype (phenotypes I and II) (HR=1.00 [0.22-4.46], p=0.99; FIG. 15). Notably, a strong and significant association was observed between breast cancer subtype and cell cycle phenotype (p<0.001). The proportion of patients with an actively cycling phenotype (phenotype III) was significantly higher in both the Her-2 (91%, 10/11) (p=0.003) and triple negative subtypes (96%, 25/26) (p<0.001) than in the luminal subtype (49%, 71/145) (FIG. 16). Whereas the proportion of hormone receptor negative tumours displaying the out-of-cycle phenotype (phenotype I) and the G1 delayed/arrested phenotype (phenotype II) was only 4% (1/26) and 9% (1/11) respectively, in the luminal subtype the proportion was 51% (74/145), of which 21% (30/145) displayed phenotype 1 and 30% (44/145) phenotype II (FIG. 16).

Discussion

Analysis of the complex and redundant pathways that control such processes as proliferation, differentiation, apoptosis and DNA damage response by global genome wide analysis is proving constrained as a prognostic tool in breast cancer (Dunkler et al., Eur J Cancer, 43:745-751, 2007). Here we have focused on the highly evolutionary conserved cell cycle machinery which lies downstream of complex signalling pathways that impact on cell cycle progression and therefore can be regarded as an integration point for information transduced through such pathways. We have shown that this novel form of multiparameter cell cycle analysis not only provides novel insights into the cell cycle kinetics of tumours but is of important prognostic significance in a range of tumour types including prostate, renal and ovarian cancer.

Our analysis of DNA replication licensing factors and mitotic regulators further characterises the unusual cell cycle state in premenopausal breast tissue. Although the growth fraction identified by the standard proliferation marker Ki67 is small, a large number of mammary epithelial cells within the TDLU express Mcm2, indicating that a large number of cells appear to be licensed and therefore "in-cycle". However, these cells fail to express markers of cell cycle progression including the S-G2-M markers geminin, Aurora A, PLK1 and the mitotic marker H3S10ph, indicating that these cells reside in a G1 arrested state. This primed, licensed state in non-proliferating breast may be an evolutionary adaptation allowing for a rapid response to pregnancy, but also that failure to down-regulate the DNA replication licensing pathway might make transition to uncontrolled cellular proliferation easier to achieve.

Our cell cycle analysis of breast cancer shows that decreasing levels of tumour differentiation and increasing genomic instability, hallmarks of the more aggressive tumours, are associated with increased levels of Mcm2, geminin, Aurora A, PLK1 and H3S10ph, indicative of an increased proportion of cells engaged in cell cycle. However, in contrast to ovary, decreasing levels of tumour differentiation and aneuploidy were not associated with accelerated cell cycle progression. Moreover, no association between tumour stage and cell cycle biomarkers was observed, again contrasting with ovary in which there were highly significant associations between Aurora A, H3S10ph and tumour FIGO stage. This implies that there are fundamental differences in the dysregulation of the cell cycle machinery between different tumour types and which may be related to different cancer genetic backgrounds.

Our analysis of breast cancer has shown that core constituents of the DNA replication licensing pathway (G1-S regulators) and mitotic machinery (G2-M regulators) are powerful independent prognostic markers in breast cancer and add value over and above the prognostic value of the NPI score alone. Intriguingly, the most powerful prognostic markers of recurrence and survival are the mitotic kinases Aurora A and PLK1, both currently a major focus of small molecule inhibitor cancer drug discovery programmes. This raises the possibility that multi-parameter cell cycle analysis on biopsy tumour samples could be used as a predictive test for small molecules targeting the cell cycle machinery. Importantly, PLK1 and Aurora A expression showed considerable overlap between grades and stage indicating that traditional clinicopathological parameters are probably inadequate for predicting therapeutic response. Our data support the concept of co-evolution of biomarker and individualised targeted therapy for the cost effective introduction of novel small molecule inhibitors into clinical practice. In addition to mechanism-based therapeutics multiparameter cell cycle analysis might also be of value in predicting response to conventional chemotherapeutic agents and ionizing radiation. Non-proliferating cells which have withdrawn from cycle have a particular significance to chemotherapy since they are immune to S phase and mitosis-linked agents. Moreover, cell cycle phase determines a tumour cell's relative radiosensitivity, with cells being more radiosensitive in G2-M phase, less sensitive in G1 and least sensitive during the latter part of S phase.

Many of the cell cycle markers studied including Ki67, Mcm2, geminin, Aurora A, PLK1 and H3S10ph were associated with breast cancer recurrence. Importantly, the effects remain statistically significant after adjusting for NPI and are therefore independent prognostic factors. However, these critical components of the cell cycle machinery lie at the convergence point of mitogenic signalling pathways downstream of immediate early and delayed response genes and the E2F transcriptional regulatory control system.

In summary, we have shown that core constituents of the cell cycle machinery, an integration point for upstream growth regulatory pathways, can greatly enhance prognostic assessment in breast cancer and provides additional information to standard clinico-pathological parameters and integrated NPI score. Aurora A and PLK1 appear to be of particular prognostic importance and may therefore have potential as predictive markers for selective mitotic kinase inhibitors that are now entering clinical trials.

Example 2

DNA Replication Licensing Factors and Aurora Kinases are Linked to Aneuploidy and Clinical Outcome in Epithelial Ovarian Cancer Study Cohort.

One hundred and forty-three patients diagnosed with EOC between Jan. 1, 1999 and Dec. 31, 2004 were identified from the Ovarian Carcinoma Database held in the Department of Oncology (University College London Hospital Gynaecological Cancer Centre, UCL Hospitals, London, UK). Patients were selected on the basis of available histologic material. Histologic specimens had been reviewed by a gynecological oncology pathologist at diagnosis and assessed for histologic subtype and nuclear grade according to WHO criteria. Most patients had been reviewed after completing treatment every 3 to 6 months for 2 years, and annually thereafter. The following clinical information was obtained directly from patients' hospital notes: date of birth, date of diagnosis, operative findings including amount of residual disease, Federation of International Obstetricians and Gynecologists (FIGO) stage based on findings at clinical examination and surgical exploration together with cytology results, CA125 values at diagnosis and relapse, performance status at start of chemotherapy, date of relapse, date of last follow-up, and date and cause of death. Of the 143 patients, 67 (47%) relapsed within the study period. Mean time to relapse among those who relapsed was 16.9 months (SD, 11.0 months; range, 0-47 months). Mean follow-up time among those who had not yet relapsed was 33.2 months (SD, 18.5 months; range 5-75 months). Thirty-four of the patients (24%) died within the study period and 107 were still alive at the last follow-up. Mean survival time among those who had died was 21.9 months (SD, 15.6 months; range 0-60 months). Mean follow-up time among those who had not yet died was 33.3 months (SD, 18.8 months; range, 5-75 months). Two patients were lost to follow-up. Ethics committee approval was obtained from the joint UCL/UCLH Committees on the Ethics of Human Research.

Antibodies.

Rabbit polyclonal antibody against human geminin was generated as described (Wharton et al. Br J Cancer; 91:262-9, 2004). Ki67 monoclonal antibody (clone MIB-1) was obtained from DAKO, Mcm2 monoclonal antibody (clone 46) was from BD Transduction Laboratories, Aurora A monoclonal antibody NCL-L-AK2 (clone JLM28) was from Novocastra Laboratories, Aurora B polyclonal antibody Ab2254 was from Abcam PLC, and histone H3 phosphorylated on serine 10 (H3S10ph) polyclonal antibody was from Upstate.

Cell Culture and Synchronization.

HeLa S3 cells (European Collection of Animal Cell Cultures 87110901) were cultured and synchronized as described (Stoeber et al. 2001 supra), Cell cycle synchronization was verified by flow cytometry of isolated nuclei as previously described (Krude et al. Cell; 88:109-19, 1997). Preparation of protein extracts and immunoblotting. HeLa S3 cells were harvested by treatment with trypsin, washed in PBS, and resuspended in lysis buffer [50 mmol/L Tris-Cl (pH 7.5), 150 mmol/L NaCl, 20 mmol/L EDTA, 0.5% NP40] at $2 \times 10^7$ cells/mL. After incubation on ice for 30 min, the lysate was clarified by centrifugation (13,000×g, 15 min, 4° C.). Lysates were separated by 4% to 20% SDS-PAGE (75 µg protein/well) and immunoblotted as previously described (Stoeber et al. 2001 supra), Blocking, antibody incubations, and washing steps were done using the following conditions: PBS/0.1% Tween 20/5% milk for Mcm2 and Aurora A, PBS/1% Tween 20/10% milk for geminin, and PBS/5% milk for Aurora B and H3S10ph.

Immunohistochemistry.

Archival formalin-fixed, paraffin-embedded tissue obtained at initial diagnosis was available for all patients, and for each specimen, a block was chosen that contained a representative sample of invasive tumour. Consecutive serial sections cut from each paraffin-embedded tissue block were used for immunohistochemistry. Three-micrometer sections were cut onto Superfrost Plus slides (Vision BioSystems), dewaxed in xylene, and rehydrated through graded alcohol to water. Tissue sections were pressure-cooked in 0.1 mol/L citrate buffer at pH 6.0 for 2 min and immunostained using the Bond Polymer Define Detection kit and Bond-X automated system (Vision BioSystems). Primary antibodies were applied at the following dilutions: Ki67 (1:100), Mcm2 (1:2,000), geminin (1:600), Aurora A (1:50), Aurora B (1:200), and H3S10ph (1:300). Coverslips were applied with Pertex mounting medium (Cell Path Ltd.). Incubation without primary antibody was used as a negative control and colonic epithelial sections as positive controls.

Protein Expression Profile Analysis.

Protein expression analysis was done by determining the labeling index of the markers in each tumour, as previously described (Shetty et al. 2005 supra. Dudderidge et al. 2005 supra). Slides were evaluated at low-power magnification (×100) to identify regions of tumour with the highest intensity of staining. From these selected areas, three to five fields at ×400 magnification were captured with a charged coupled device camera and analysis software (SIS). Images were subsequently printed for quantitative analysis, which was undertaken with the observer unaware of the clinicopathologic variables. Both positive and negative cells within the field were counted and any stromal or inflammatory cells were excluded. Criteria for the identification of positive cells were dependent on the biomarkers for Ki67, Mcm2, geminin, Aurora B, and H3S10ph; cells with any degree of nuclear staining were scored positive. For Aurora A, cells with any degree of nuclear or cytoplasmic staining were scored positive (Gritsko et al., 2003 supra). A minimum of 500 cells were counted for each case. The labeling index was calculated using the following formula: labeling index=number of positive cells/total number of cells×100. Reassessment of 10 randomly selected cases by an independent assessor showed high levels of agreement.

DNA Image Cytometry.

For each case, one 40-μm section of paraffin embedded tissue obtained from the same block as that assessed by immunohistochemistry was used to prepare nuclei as described (Sudbo et al. 2001 supra. Haroske et al. 1997 supra). The Fairfield DNA Ploidy System (Fairfield Imaging, Ltd.) was used for image processing, analysis, and classification as previously described (Sudbo et al. 2001 supra). Lymphocytes and plasma cells were included as internal controls and 40-μm sections of high-grade bladder tumour and normal colonic tissue as external controls for aneuploid and diploid populations, respectively. Histograms were classified according to published criteria (Sudbo et al. 2001 supra. Haroske et al. 1998 supra). Histograms were classified by two independent assessors with a high level of agreement without knowledge of clinicopathologic variables. For statistical analysis, tetraploid and polyploid tumours were grouped together with aneuploid tumours.

Statistical Analysis.

Spearman's rank correlation coefficient was used to examine associations between biomarkers. Relationships between biomarker expression and tumour grade, stage, and ploidy status were assessed using nonparametric Jonckheere-Terpstra and Mann-Whitney U tests as appropriate. Data were then summarized as the median value and interquartile range of labeling indices observed across the cohort. Analysis of disease-free and overall survival data was carried out using Kaplan-Meier plot (using tertiles for biomarkers), log-rank test, and Cox regression (treating biomarkers as continuous variables unless stated otherwise). For each biomarker, the cohort was divided into tertile groups on the basis of the labeling index. Within each tertile group, the proportion remaining that was either disease-free or alive, for disease-free and overall survival, respectively, was calculated using the Kaplan-Meier method. Hazard ratios (HR) with 95% confidence intervals (95% CI) for biomarkers were first estimated unadjusted, and then adjusted for age, grade and stage. Patients with incomplete data were excluded from the multivariate analysis. Candidate biomarkers are listed in Supplementary Table S1. All tests were two-sided and used a significance level of 0.05 and no allowances were made for multiple hypothesis testing. Analysis was carried out using SPSS12.0 for Windows (SPSS, Inc.).

Results

Validation of Biomarker Multiparameter Analysis and its Biological Implications.

Figure 10:
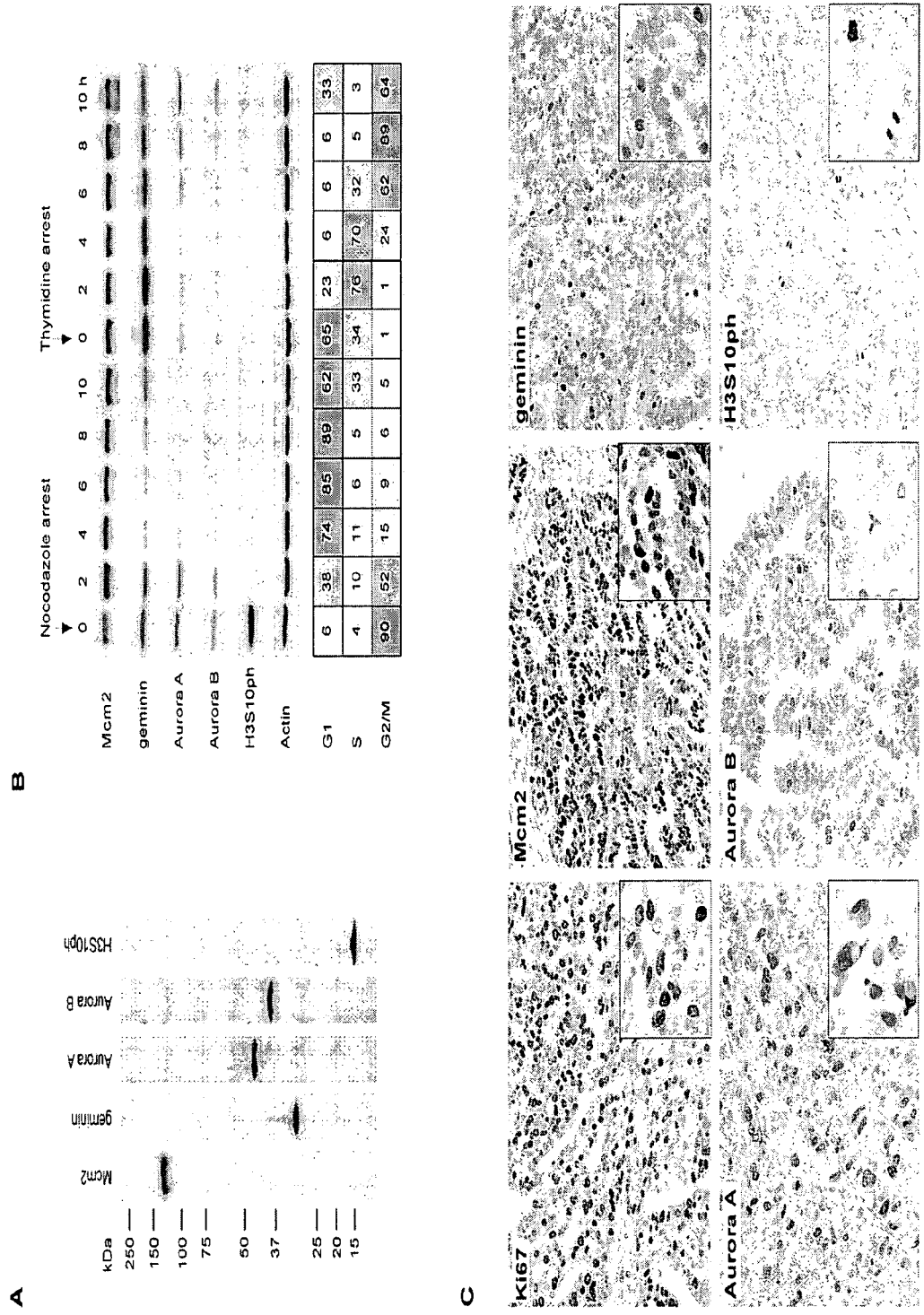
FIG. 10 shows (A) Immunoblots of asynchronous HeLa S3 total cell lysates with antibodies against Mcm2, geminin, Aurora A, Aurora B and H3S10ph. (B) Immunoblots of biomarkers and actin (loading control) in total cell lysates from synchronized HeLa S3 cells. FACS profiles of synchronized HeLa S3 cells at 2-hour intervals. (C) Photomicrographs of paraffin-embedded tissue sections of epithelial ovarian carcinoma (EOC) immunohistochemically stained with antibodies against Ki67, Mcm2, geminin, Aurora A, Aurora B and H3S10ph. Original magnification, 400×; inset, 1000×.

The monospecificity of antibodies against Mcm2, geminin, Aurora A, Aurora B, and H3S10ph was confirmed in total cell extracts from asynchronous HeLa S3 cells by detection of a single protein with a molecular mass consistent with the reported electrophoretic mobility of the corresponding human antigen (FIG. 10A). HeLa S3 cells were selected in the first instance for in vitro studies as this line has well characterized cell cycle phase transit times and established synchronization protocols. Total cell lysates from synchronized cells were immunoblotted with the characterized antibodies (FIG. 10B). Mcm2 levels did not vary significantly during passage through the cell cycle, whereas geminin expression was restricted to S-G2-M. Aurora A levels increased during S phase and peaked during mitosis, with degradation occurring 2 to 4 h after release from mitotic arrest. Similarly, Aurora B levels were negligible during G1 phase, increased gradually during S phase to reach a peak during G2-M, and decreased after mitosis. The presence of H3S10ph was restricted to mitosis, consolidating the rationale for its use as a mitotic marker. Identical cell cycle-dependent expression of these biomarkers was observed in synchronized SK-OV 3 ovarian cancer cells (data not shown). Because Ki67 is expressed throughout the cell cycle in proliferating cells and geminin expression is restricted to the S-G2-M phase, we have proposed that the geminin/Ki67 ratio may be used as an indicator of the relative length of G1, and therefore, the rate of cell cycle progression. The data described above confirm that cell cycle-dependent expression of Aurora A and Aurora B also enables the use of their ratios with Ki67 as indicators of cell cycle progression. Increased geminin expression is always restricted to the S-G2-M phase, even in highly aggressive tumours. Our in vitro findings therefore also indicate that an increase in the relative ratio between Aurora A or Aurora B and geminin (ratio>1) would be indicative of overexpression of the kinase during the cell cycle. To assess the prognostic significance of our in vitro findings and their biological implications in EOC, we analysed the expression of biomarkers in a series of 143 cases (FIG. 10C). Protein expression was also studied in five cases of normal ovarian tissue. Expression of the biomarkers was extremely low (<4%) in normal ovarian surface epithelium, in keeping with its lowered proliferative capacity (data not shown). By contrast, EOC showed high levels of biomarker expression, indicative of cell cycle re-entry and proliferation.

Next, we examined the correlations between pairs of biomarkers across the tumour series. The expression levels of Aurora A and Aurora B showed a strong positive correlation with those of their substrate H3S10ph [Spearman correlation, 0.57 (95% CI, 0.45-0.67) and 0.52 (95% CI, 0.39-0.63), respectively]. The expression levels of Mcm2, geminin, and H3S10ph were strongly positively correlated with Ki67 levels [Spearman correlation, 0.73 (95% CI, 0.64-0.8); 0.74 (95% CI, 0.66-0.81); and 0.52 (95% CI, 0.39-0.63), respectively], supporting their role as proliferation markers. Notably, the geminin/Ki67 and Aurora A/Ki67 ratios were positively, but less strongly, correlated with H3S10ph [Spearman correlation, 0.25 (95% CI, 0.09-0.40) and 0.42 (95% CI, 0.27-0.55), respectively], which reflects changes in the relative length of G1 as opposed to prolonged S-G2-M transit times that might arise through the activation of intra-S or G2-M checkpoint pathways.

This is consistent with a tumour mass only becoming clinically detectable after the tumour cell has undergone a major proportion of its population doublings, approximately 30 doublings out of a total of 40. This number of population doublings represents the maximum mass compatible with life, a point in somatic clonal evolution in which most cell cycle checkpoint mechanisms have been overridden.

Relationship Between Biomarkers, Tumour DNA Ploidy Status, and Clinicopathologic Characteristics.

The clinicopathologic characteristics of the study cohort are summarized in Table 10. To investigate the relationship between the biomarkers and genomic instability, we linked their expression profiles to tumour DNA content. There was a highly significant association between the expression levels of all of the biomarkers and several biomarker/Ki67 ratios and genomic instability (Table 11), reflecting an increased proportion of cycling cells and accelerated cell cycle progression in aneuploid tumours as compared with diploid tumours.

Figure 11:
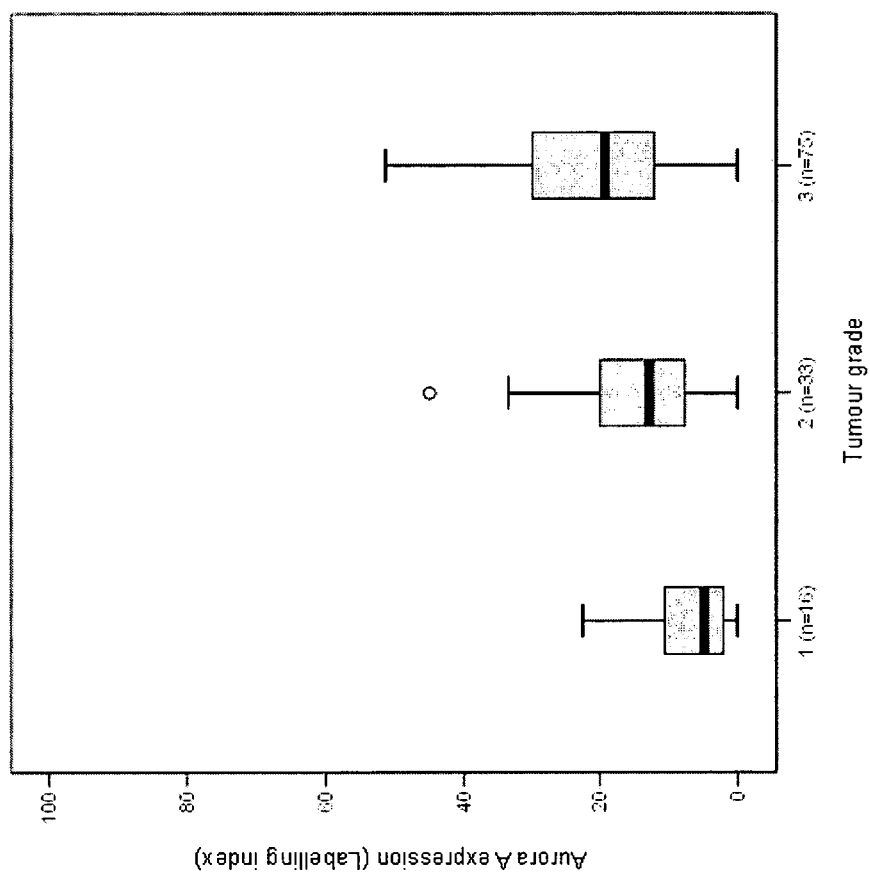
FIG. 11 shows Aurora A expression across tumour grades (EOC series).

All six biomarkers were also strongly associated with tumour grade (Table 12); however, there is some overlap in the distributions of biomarker levels between grades (e.g., Aurora A levels; FIG. 11). These data confirm an increasing proportion of cycling cells with increasing tumour anaplasia, but also indicate that the biomarkers do not fully distinguish between grades for all patients within each grade.

In keeping with these findings, a highly significant association between tumour grade and ploidy status was found ($p<0.001$). The ratios among geminin/Ki67, Aurora A/Ki67, Aurora B/Ki67, and H3S10ph/Ki67 were also significantly associated with tumour differentiation (Table 12), indicative of an accelerated rate of cell cycle progression in high-grade tumours. By contrast, and consistent with our findings in other tumour types, the Mcm2/Ki67 ratio decreased with increasing tumour grade (Table 12), reflecting a shift in the proportion of DNA replication licensed, but non-proliferating cells in well-differentiated tumours to actively cycling cells in poorly differentiated tumours. The positive correlation between geminin expression and increasing tumour anaplasia and genomic instability (Tables 11 and 12) indicates that this licensing repressor does not behave as a tumour suppressor in EOC.

A significant association was found between Aurora A, H3S10ph, Aurora A/Ki67, H3S10ph/Ki67 and tumour stage (Table 13). This suggests that Aurora A dysregulation might be a key event in early epithelial ovarian tumourigenesis and progression to advanced stage disease. Furthermore, advanced stage disease was significantly associated with an increase in the Aurora A/geminin ratio ($p=0.04$; Table 13), also supporting a link between Aurora A dysregulation and tumour progression.

Figure 12:
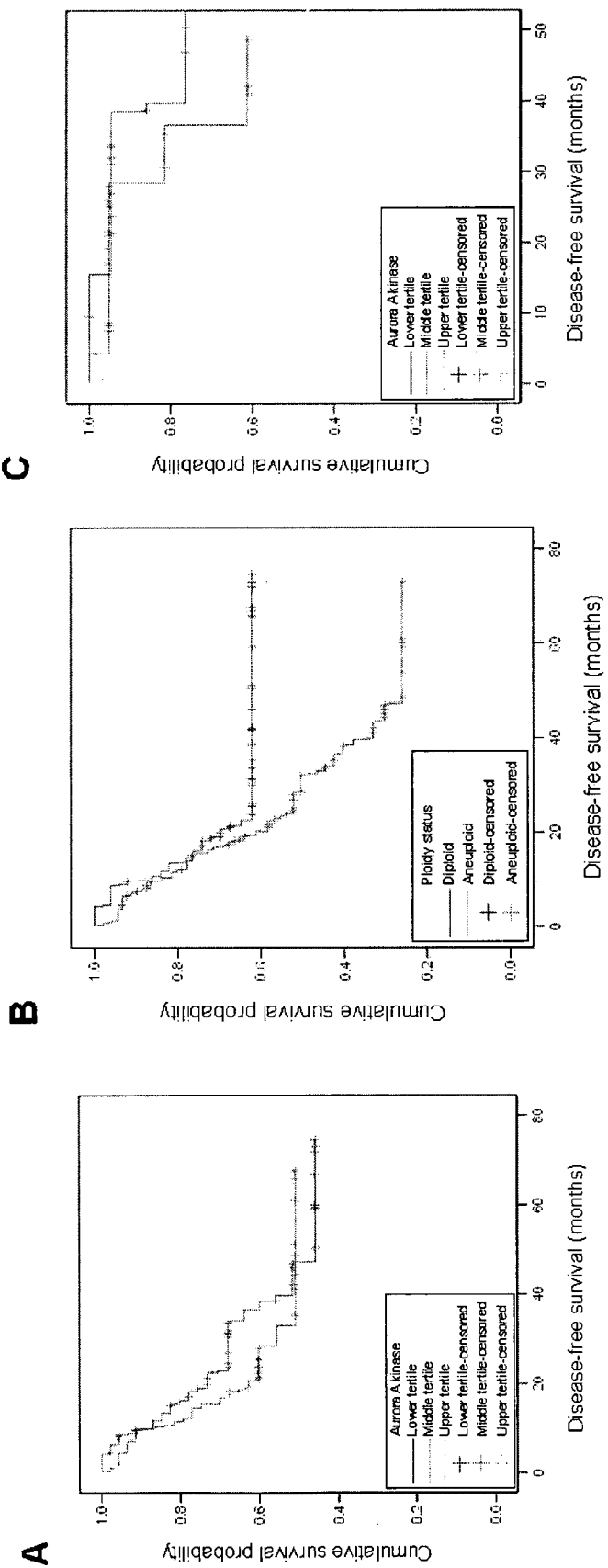
FIG. 12 shows Kaplan-Meier curves showing association between Aurora A, tumour ploidy status, and patient survival for EOC series. (A) Aurora A (lower tertile <11.3%, middle tertile 11.3-21.3%, upper tertile >21.3%) and disease-free survival across whole series; log rank test, p=0.01. (B) Tumour ploidy status and disease-free survival across whole series; log rank test, p=0.03. (C) Aurora A (lower tertile <8.7%, middle tertile 8.7-19.6%, upper tertile >19.6%) and disease-free survival in early stage subgroup; log rank test, p=0.004. (D) Tumour ploidy status and disease-free survival in early stage subgroup; log rank test, p=0.04. (E) Aurora A (lower tertile <8.7%, middle tertile 8.7-19.6%, upper tertile >19.6%) and overall survival in early stage subgroup; log rank test, p=0.01. (F) Tumour ploidy status and overall survival in early stage subgroup; log rank test, p=0.08.
Figure 12:
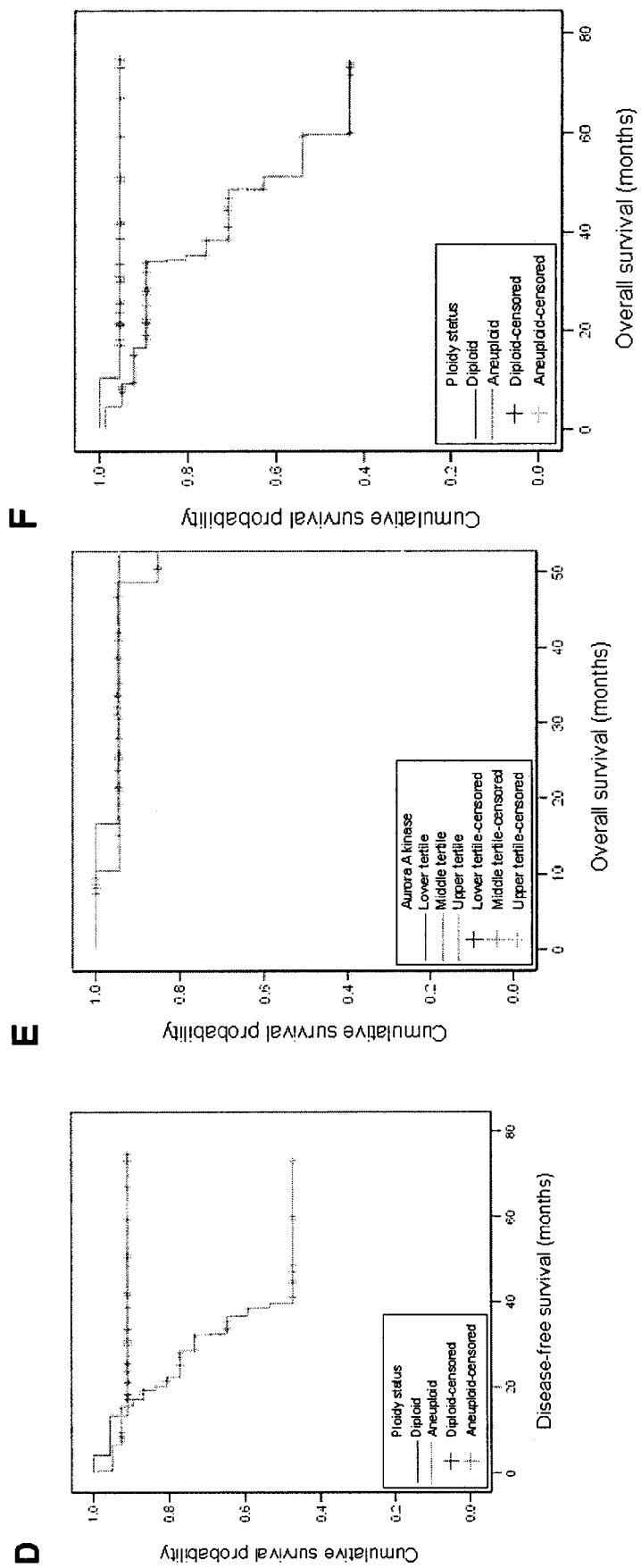

Relationship Between Biomarkers, Tumour DNA Ploidy Status, and Patient Outcome
Univariate Analysis Aurora A ($p=0.01$; FIG. 12A), Aurora A/Ki67, Aurora B/Ki67, and H3S10ph (Table 14) were all significantly associated with shorter disease-free survival but not overall survival. Patient age, tumour grade, and stage were also predictive of disease-free survival, with younger patients, well-differentiated tumours, and particularly, early stage disease having a significantly longer time-to-relapse [HR, 1.02 (1.00-1.05), $p=0.05$; HR, 1.59 (1.03-2.45), $p=0.04$; HR, 2.07 (1.58-2.71), $p<0.0001$, respectively]. Patient age and tumour stage also predicted overall survival [HR, 1.05 (1.02-1.09), $p=0.003$; HR, 3.21 (1.33-7.79), $p=0.01$, respectively] but tumour grade did not ($p=0.70$), emphasizing the limitations of the current grading systems. Tumour ploidy status also significantly correlated with disease-free survival [HR, 1.80 (1.05-3.08), $p=0.03$; FIG. 12B], with a trend towards shorter overall survival in patients with aneuploid tumours, although this did not reach statistical significance [HR, 1.95 (0.88-4.31), $p=0.10$].

We subdivided our series into two groups; early stage disease (FIGO stages I and II) and advanced stage disease (FIGO stages III and IV) to more precisely define the specific subgroups for which the biomarkers may have particular prognostic importance. Both Aurora A and the Aurora A/Ki67 ratio were strongly predictive of shorter disease-free survival [HR, 1.72 (1.19-2.48), $p=0.004$ (FIG. 12C); HR, 1.59 (1.13-2.24), $p=0.008$, respectively] and overall survival [HR, 1.81 (1.14-2.87), $p=0.01$ (FIG. 12E); HR, 1.68 (1.11-2.54), $p=0.01$, respectively] in the early stage subgroup. This association was not found in the advanced stage subgroup [HR, 1.06 (0.81-1.37), $p=0.67$; HR, 1.04 (0.90-1.20), $p=0.58$ for disease-free survival; and HR, 0.88 (0.58-1.33), $p=0.88$; HR, 0.89 (0.69-1.15), $p=0.36$ for overall survival, respectively]. Tumour ploidy status also predicted disease-free survival [HR, 4.58 (1.04-20.19), $p=0.04$; FIG. 12D], with a trend towards shorter overall survival in patients with aneuploid tumours [HR, 6.34 (0.82-49.18), $p=0.08$; FIG. 12D] in the early stage subgroup. However, it lost its predictive value in the advanced stage subgroup [HR, 1.47 (0.81-2.66), $p=0.21$ and HR, 1.36 (0.55-3.33), $p=0.5$ for disease-free survival and overall survival, respectively].

Multivariate Analysis

Cox regression survival analysis showed that tumour stage was the only significant independent predictor of disease-free survival [HR, 2.06 (1.49-2.85), $p<0.0001$]. Patient age and tumour stage were independent predictors of overall survival, with older patients and advanced stage tumours having shorter overall survival times [HR, 1.05 (1.01-1.09), $p=0.007$; HR, 3.19 (1.31-7.75), $p=0.01$, respectively]. Although several biomarkers were significant prognostic factors in univariate analysis, none was a significant predictor of disease-free or overall survival after adjustment for age, grade, and stage. This is due partly to the highly significant associations between the biomarkers and tumour grade and stage, making it difficult to separate their independent effects.

Discussion

This study was undertaken to gain further insight into biological markers of EOC that may be of prognostic and predictive value and could lead to a greater understanding of its pathogenesis. Our findings show that the Mcm2 and geminin replication licensing factors, and the Aurora A and B kinases, together with their substrate H3S10ph, are of prognostic value in EOC. The association found between tumour differentiation and this set of biomarkers has implications for their use as proliferation markers with potential for further improvements in the current grading system. Our multiparameter analysis shows that it could also be used to provide information about cell cycle progression in patient tumour samples, data that translate into important prognostic information.

These findings are in keeping with analysis of licensing factors in breast and renal cell cancer. Furthermore, the highly significant association found between this set of biomarkers and tumour ploidy status suggests that dysregulation of the licensing machinery and mitotic kinases is intricately linked to the development of genomic instability in EOC. Aurora A plays a regulatory role in several key stages of the G2-M transition. Here, we report an intriguing link between aberrant regulation of Aurora A and EOC progression. Our data show highly significant associations between Aurora A, H3S10ph and tumour FIGO stage, supporting a view that Aurora A dysregulation might be an early event in epithelial ovarian carcinogenesis and suggesting that its dysregulation might play a role in the progression to advanced disease.

In line with these findings, the Aurora A/geminin ratio is significantly higher in advanced stage tumours, which also suggests that Aurora A overexpression might play a role in or might be a result of tumour progression. In vivo, it is likely that such overexpression is regulated by not only gene amplification but also other mechanisms such as transcriptional activation and suppression of protein degradation. Our data suggest that multiparameter analysis of Aurora A and H3S10ph allows molecular staging which could be used to complement clinical staging methods. FIGO stage is an important prognostic indicator in EOC, however, surgical and radiological staging methods have their limitations. Randomized trials have shown that adjuvant chemotherapy is of particular benefit in suboptimally staged patients with stage I disease. However, in a recent large randomized controlled trial, only 34% of patients were optimally staged according to guidelines (Vegote I et al Curr. Op. Oncol. 2003; 15:452-5). In those patients who were inadequately staged, these biomarkers might provide supportive evidence of either true stage I or more advanced disease, assisting a decision about the use of adjuvant chemotherapy. The findings of the ICON 1/ACTION trials suggested a small overall benefit for adjuvant chemotherapy (Trimbos J B et al J Natl Cancer Inst 2003; 95:105-12), but it remains unclear which adequately staged patients with stage I disease really need chemotherapy.

Aurora A, H3S10ph, and genomic instability are also significant predictors of disease-free survival in this study cohort. Further subgroup analysis showed that Aurora A and tumour ploidy status are predictive of disease-free survival (with Aurora A expression also predicting overall survival) in early disease. However, this association was reduced when prognostic factors such as age and stage were taken into account. By contrast, these variables lost their predictive value in advanced disease [e.g., HR for Aurora A dropped from 1.72 (1.19-2.48) in early stage disease to 1.06 (0.81-1.37) for advanced stage disease], suggesting that other biological factors may take precedence in influencing relapse and outcome in these patients. In addition, the complexity and heterogeneity of treatment regimens might mask the predictive value of these biomarkers in advanced stages.

Taken together, our data are supportive of a biological mechanism by which Aurora A dysregulation at an early point during tumourigenesis might contribute to genetic instability, resulting in aggressive tumours and shorter survival in a subgroup of patients with early stage disease.

DNA replication licensing factors and mitotic kinases are critical regulators of cell cycle progression, and thus, are the focus of current therapeutic drug development programs. Here, we have shown that multiparameter expression analysis of core regulators of the G1-S and G2-M transitions allows the assessment of the rate of cell cycle progression in individual patient tumour samples, variables linked to the biological behavior of these tumours. This type of analysis could be used as a predictive test for small molecules targeting the cell cycle machinery or upstream growth signal transduction pathways that accelerate cell cycle progression. Moreover, the observation that Aurora A expression does not fully distinguish between grades shows that traditional clinicopathologic variables do not always allow the prediction of therapeutic response, supporting the concept of coevolution of biomarker and individualized targeted therapy. In view of the recent development of specific Aurora kinase inhibitors, our data have important implications—prognostic, predictive, and therapeutic—for the use of Aurora A as a biomarker and potential therapeutic target.

BIBLIOGRAPHY

Barkley et al., Exp Cell Res 313:3789-3799, 2007
Blow and Hodgson, Trends Cell Biol 12:72-78, 2002
Dudderidge et al. Clin Cancer Res 11:2510-7, 2005
Dudderidge et al., Clin Cancer Res 11:25110-2517, 2005
Dunkler et al. Eur J Cancer, 43:745-751, 2007
Eward at al., J Cell Sci 117:5875-5886, 2004
Gonzalez et al., J Pathol 204:121-130, 2004
Gritsko et al. Clin Cancer Res 9:1420-6, 2003
Haroske et al. Anal Cell Pathol 1998; 17:189-200, 1997
Kingsbury at al., Exp Cell Res 309:56-67, 2005
Krude et al. Cell; 88:109-19, 1997
Shetty et al. Br J Cancer 93:1295-300, 2005
Shetty et al., Br J Cancer 93:1295-1300, 2005
Stoeber et al. J Cell Sci, 114:2027-41, 2001
Stoeber et al., EMBO J 17:7219-7229, 1998
Stoeber et al., J Cell Sci 114:2027-2041, 2001
Sudbo et al., N Engl J Med 344:1270-8, 2001
Wharton et al. Br J Cancer; 91:262-9, 2004
Williams and Stoeber, Curr Opin Cell Biol 19:672-679, 2007

TABLE 1

Proliferation targets of chemotherapeutic agents

| Drug | Target | Mechanism of action | Phase affected |
|---|---|---|---|
| 5-fluorouracil | Thymidylate synthetase | Ribonucleotide depletion | S |
| Hydroxyurea | Ribonucleotide reductase | Ribonucleotide depletion | S |
| Methotrexate | Dihydrofolate reductase | Ribonucleotide depletion | S |
| Doxorubicin | Topoisomerase II | Stabilization of Topoisomerase II-DNA complex, which leads to replication arrest | S |
| Etoposide | Topoisomerase II | Stabilization of Topoisomerase II-DNA complex, which leads to replication arrest and strand breakage | S or G2/M |
| Cisplatin | DNA | Intra-strand crosslinking, which leads to replication arrest | G1/S and G2/M |
| Taxol | Tubulin | Stabilization of microtubules | G2/M |
| Flavopiridol | CDK1, CDK2, CDK4, CDK6 and CDK7 | Inhibition of CDKs by interfering with ATP-binding | Several |
| Staurosporine (UCN-01) | CDK1 | Inappropriate activation of CDK1 by phosphorylation | G2/M abrogated |
| ZM447439 | Aurora kinase-A and -B | Inhibit histone H3 phosphorylation on serine 10 | G2/M |
| BI2536 | Plk-1 | Arrests cells in prometaphase and initiates cyclin A destruction | M |

CDK, cyclin-dependent kinase

TABLE 2

Patient characteristics

| | | Frequency (number) |
|---|---|---|
| Age (years) | <40 | 7% (12) |
| | 40-49 | 19% (34) |
| | 50-59 | 28% (51) |
| | 60-69 | 22% (41) |
| | 70+ | 24% (44) |
| Size (mm) | <11 | 9% (16) |
| | 11-20 | 33% (60) |
| | 21-30 | 30% (54) |
| | 31-40 | 16% (29) |
| | >40 | 13% (23) |
| Lymph node stage | Negative nodes | 53% (97) |
| | Positive, 1 to 3 | 22% (40) |
| | Positive, 4 or more | 18% (32) |

TABLE 2-continued

Patient characteristics

| | | Frequency (number) |
|---|---|---|
| | Mucinous | 2% (4) |
| | Mixed | 5% (9) |
| | Micropap | 1% (1) |
| Breast cancer recurrence | Yes | 26% (48) |
| | No | 68% (124) |
| | Unknown | 6% (10) |
| Breast cancer death | Yes | 14% (26) |
| | No | 80% (146) |
| | Unknown | 6% (10) |
| Recurrence follow-up (years) | | 632 (3.8 per subject) |
| Survival follow-up (years) | | 684 (4.1 per subject) |

TABLE 3

Relationship between biomarkers and tumour differentiation

| | Grade 1 (n = 24) | Grade 2 (n = 80) | Grade 3 (n = 78) | p-value[†] |
|---|---|---|---|---|
| Ki67* | 7.3 (2.4-17.6) | 16.6 (8.05-30.9) | 40.2 (25-66.9) | <0.001 |
| Mcm2* | 45.8 (17.1-65.6) | 57.8 (29.3-83) | 92.3 (70.0-100.0) | <0.001 |
| Geminin* | 2.0 (0.9-5.8) | 6.5 (3.3-10.6) | 17.4 (10.6-24.8) | <0.001 |
| ER* | 100.0 (100.0-100.0) | 100.0 (94.0-100.0) | 30.2 (0.0-100.0) | <0.001 |
| PR* | 93.5 (52.8-100.0) | 87.9 (38.0-100.0) | 0.0 (0.0-90.3) | <0.001 |
| Aurora A* | 1.7 (0.4-4.1) | 4.3 (1.4-7.2) | 11.7 (6.2-20.2) | <0.001 |
| Plk1* | 2.3 (0.3-5) | 5.3 (2.6-9.7) | 14.2 (8.9-21.7) | <0.001 |
| H3phS10* | 0.2 (0.03-0.5) | 0.8 (0.3-1.6) | 2.5 (1.4-3.8) | <0.001 |
| Mcm2/Ki67 | 4.48 (2.74-6.35) | 2.77 (2.04-5.00) | 1.71 (1.25-3.00) | <0.001 |
| Geminin/Ki67 | 0.36 (0.21-0.60) | 0.36 (0.25-0.52) | 0.38 (0.29-0.58) | 0.29 |
| Aurora A/Ki67 | 0.26 (0.11-0.42) | 0.24 (0.13-0.33) | 0.29 (0.16-0.42) | 0.11 |
| Plk1/Ki67 | 0.27 (0.12-0.51) | 0.29 (0.22-0.50) | 0.34 (0.26-0.50) | 0.09 |
| H3phS10/Ki67 | 0.045 (0.01-0.08) | 0.046 (0.02-0.09) | 0.060 (0.04-0.09) | 0.04 |

[†]Jonckheere-Terpstra test
*Labelling index (expressed as percentages)
[‡]Median (inter-quartile range)

TABLE 2-continued

Patient characteristics

| | | Frequency (number) |
|---|---|---|
| | Unknown | 7% (13) |
| Grade | 1 | 13% (24) |
| | 2 | 44% (80) |
| | 3 | 43% (78) |
| NPI score | mean (sd) 4.49 (1.31) | |
| | <3.4 | 18% (32) |
| | 3.4-5.4 | 51% (93) |
| | >5.4 | 24% (44) |
| | Unknown | 7% (13) |
| Ploidy status | Diploid | 47% (86) |
| | Aneuplod | 50% (90) |
| | Unknown | 3% (6) |
| Her2 | 0 | 59% (108) |
| | 1+ | 18% (33) |
| | 2+ | 7% (13) |
| | 3+ | 15% (28) |
| ER | positive (100%) | 53% (96) |
| | negative (<100%) | 47% (86) |
| PR | positive (<63%) | 50% (91) |
| | negative (>63%) | 50% (91) |
| ER positive PR positive | | 37% (67) |
| Either ER or PR negative | | 63% (115) |
| Lymphovascular invasion | Absent | 47% (86) |
| | Present | 38% (69) |
| | Unknown | 15% (27) |
| Tumour type | Invasive ductal | 78% (142) |
| | Lobular | 14% (26) |

TABLE 4

Relationship between biomarkers and tumour DNA ploidy status

| Biomarker | Aneuploid (n = 90) | Diploid (n = 86) | p-value[†] |
|---|---|---|---|
| Ki67* | 30.0 (16.8-53.1) | 17.5 (7.2-33.1) | <0.001 |
| Mcm2* | 75.8 (48.8-96.7) | 63.1 (31.2-84.4) | 0.009 |
| Geminin* | 11.5 (5.9-21.9) | 6.9 (2.4-12.2) | <0.001 |
| ER* | 96.9 (8.0-100.0) | 100.0 (65.7-100.0) | 0.054 |
| PR* | 59.1 (0.0-97.0) | 69.3 (0.0-100.0) | 0.12 |
| Aurora A* | 7.3 (3.5-14.9) | 4.1 (1.0-8.4) | <0.001 |
| Plk1* | 9.8 (4.8-15.7) | 7.1 (2.1-11.1) | 0.002 |
| H3phS10* | 1.78 (0.78-2.89) | 0.70 (0.22-1.7) | <0.001 |
| Mcm2/Ki67 | 2.16 (1.43-3.40) | 2.85 (1.97-4.99) | 0.004 |
| Geminin/Ki67 | 0.38 (0.25-0.58) | 0.36 (0.28-0.54) | 0.74 |
| Aurora A/Ki67 | 0.28 (0.15-0.40) | 0.25 (0.12-0.42) | 0.40 |
| Plk1/Ki67 | 0.32 (0.22-0.48) | 0.30 (0.22-0.57) | 0.65 |
| H3phS10/Ki67 | 0.053 (0.03-0.09) | 0.050 (0.02-0.10) | 0.48 |

[†]Mann-Whitney Test
*Labelling index (expressed as percentages)
[‡]Median (inter-quartile range)

TABLE 5

Relationship between biomarkers and lymph node stage

| | Negative (n = 97) | Positive (n = 72) | [†]p-value |
|---|---|---|---|
| Ki67* | 22.7 (9.5-43.3) | 24.8 (11.1-47.3) | 0.49 |
| Mcm2* | 70.3 (36.2-90.1) | 71.9 (42.2-98) | 0.25 |

TABLE 5-continued

Relationship between biomarkers and lymph node stage

|  | Negative (n = 97) | Positive (n = 72) | †p-value |
|---|---|---|---|
| Geminin* | 7.9 (3.6-16.3) | 10.4 (5.1-18.2) | 0.22 |
| ER* | 100.0 (60.6-100.0) | 90.7 (0.0-100.0) | 0.007 |
| PR* | 74.3 (4.5-100.0) | 31.3 (0.0-96.1) | 0.005 |
| Aurora A* | 5.3 (1.5-10.8) | 7.0 (2.9-14.0) | 0.16 |
| Plk1* | 7.5 (3.3-14.3) | 9.2 (4.2-14.7) | 0.22 |
| H3phS10* | 0.94 (0.37-2.38) | 1.67 (0.68-2.93) | 0.02 |
| Mcm2/Ki67 | 2.57 (1.54-3.77) | 2.25 (1.64-4.78) | 0.92 |
| Geminin/Ki67 | 0.36 (0.25-0.56) | 0.38 (0.29-0.56) | 0.38 |
| AuroraA/Ki67 | 0.26 (0.12-0.38) | 0.29 (0.17-0.48) | 0.15 |
| Plk1/Ki67 | 0.28 (0.22-0.48) | 0.37 (0.22-0.52) | 0.20 |
| H3phS10/Ki67 | 0.046 (0.02-0.08) | 0.061 (0.04-0.10) | 0.02 |

†Mann-Whitney Test
*Labelling index (expressed as percentages)
‡Median (inter-quartile range)

TABLE 6

Relationship between biomarkers and NPI

|  | Expression value defining the marker's median | Mean NPI Below the marker's median | Mean NPI Above the marker's median | Correlation between and the marker NPI† |
|---|---|---|---|---|
| Ki67* | 24.0 | 4.13 | 4.86 | +0.42, p < 0.001 |
| Mcm2* | 70.7 | 4.10 | 4.88 | +0.40, p < 0.001 |
| Geminin* | 9.0 | 4.00 | 4.99 | +0.44, p < 0.001 |
| ER* | 99.9 | 4.97 | 4.05 | −0.39, p < 0.001 |
| PR* | 63.0 | 4.78 | 4.19 | −0.34, p = 0.005 |
| Aurora A* | 6.10 | 4.09 | 4.87 | +0.39, p < 0.001 |
| Plk1* | 8.40 | 3.97 | 5.01 | +0.46, p < 0.001 |
| H3phS10 | 1.25 | 3.95 | 5.01 | +0.47, p < 0.001 |
| Mcm2/Ki67 | 2.43 | 4.72 | 4.28 | −0.24, p = 0.02 |
| Geminin/Ki67 | 0.370 | 4.44 | 4.57 | +0.05, p = 0.53 |
| AuroraA/Ki67 | 0.263 | 4.33 | 4.66 | +0.14, p = 0.07 |
| Plk1/Ki67 | 0.310 | 4.33 | 4.68 | +0.12, p = 0.12 |
| H3phS10/Ki67 | 0.05087 | 4.23 | 4.76 | +0.20, p = 0.01 |

*Labelling index (expressed as percentages)
†non-parametric Spearman correlation coefficient

TABLE 7

Relationship between biomarkers and HER2 status

|  | 0 (n = 108) | 1+ (n = 33) | 2+ (n = 13) | 3+ (n = 28) | p-value† |
|---|---|---|---|---|---|
| Ki67* | 21.4 (9.5-43.9) | 22.0 (7.2-35.8) | 24.6 (10.2-52.1) | 32.2 (19.7-48.2) | 0.17 |
| Mcm2* | 70.5 (35.0-94.2) | 63.3 (38.9-80.1) | 75.0 (28.7-90.0) | 78.3 (54.8-95.6) | 0.67 |
| Geminin* | 8.4 (3.3-16.9) | 7.9 (4.0-13.3) | 10.6 (4.7-17.9) | 15.7 (7.8-21.7) | 0.056 |
| ER* | 100.0 (15.2-100.0) | 100.0 (71.0-100.0) | 96.4 (61.6-100.0) | 70.0 (0.0-100.0) | 0.12 |
| PR* | 81.2 (0.0-100.0) | 58.4 (0.4-95.1) | 45.8 (15.0-97.4) | 0.0 (0.0-52.6) | <0.001 |
| Aurora A* | 5.8 (2.0-12.3) | 6.0 (1.0-11.8) | 5.9 (1.1-9.6) | 8.9 (4.5-13.1) | 0.43 |
| Plk1* | 7.5 (3.3-13.8) | 6.1 (3.4-12.5) | 10.2 (2.8-13.4) | 11.2 (8.8-17.0) | 0.073 |
| H3phS10* | 0.9 (0.34-2.67) | 1.0 (0.46-2.60) | 1.7 (0.72-2.39) | 1.9 (0.98-2.82) | 0.044 |
| Mcm2/Ki67 | 2.57 (1.51-4.62) | 2.96 (1.55-5.62) | 2.22 (1.25-3.76) | 2.27 (1.67-2.70) | 0.38 |
| Geminin/Ki67 | 0.37 (0.26-0.55) | 0.35 (0.25-0.52) | 0.43 (0.21-0.69) | 0.37 (0.32-0.54) | 0.60 |
| Aurora A/Ki67 | 0.26 (0.15-0.39) | 0.29 (0.13-0.44) | 0.27 (0.11-0.38) | 0.25 (0.15-0.41) | 0.79 |
| Plk1/Ki67 | 0.30 (0.21-0.48) | 0.30 (0.23-0.55) | 0.34 (0.16-0.54) | 0.33 (0.25-0.50) | 0.51 |
| H3phS10/Ki67 | 0.050 (0.03-0.09) | 0.062 (0.03-0.12) | 0.066 (0.03-0.08) | 0.050 (0.04-0.08) | 0.47 |

†Jonckheere-Terpstra Test
*Labelling index (expressed as percentages)
‡Median (inter-quartile range)

TABLE 8

Relationship of HER2 status and ploidy status with NPI

|  | Mean NPI | Difference in NPI means (95% CI), p-value |
|---|---|---|
| Ploidy |  |  |
| Aneuploid (n = 83) | 4.67 | Difference = 0.33 (−0.07 to +0.74), |
| Diploid (n = 81) | 4.33 | p = 0.11* |
| HER2 |  |  |
| 0 (n = 101) | 4.35 | Mean NPI is higher per category |
| 1+ (n = 31) | 4.44 | of HER2 by 0.22 (0.04 to 0.40), |
| 2+ (n = 11) | 4.53 | p = 0.014† |
| 3+ (n = 26) | 5.09 |  |

*Unpaired t-test
†Linear regression test for linear trend

TABLE 9

Effect of NPI on Recurrence and on Cancer death

|  | Recurrence rate | Cancer death rate |
|---|---|---|
| NPI |  |  |
| <3.4 | 3% (1/30) | 3% (1/30) |
| 3.4-5.4 | 20% (17/87) | 7% (6/87) |
| >5.4 | 54% (22/41) | 34% (14/41) |
| HR (95% CI) | 1.79 (1.46 to 2.20), p < 0.001 | 2.18 (1.63 to 2.93), p < 0.001 |
| HR after adjusting for age | 1.81 (1.47 to 2.23), p < 0.001 | 2.15 (1.61 to 2.88), p < 0.001 |

TABLE 10

Patient characteristics

|  |  | n (%) |
|---|---|---|
| Age (years) | mean: 61 range: 20-88 | 143 |

TABLE 10-continued

Patient characteristics

| | | n (%) |
|---|---|---|
| Histological grade (n = 124) | 1 (well-differentiated) | 16 (13%) |
| | 2 (moderately-differentiated) | 33 (27%) |
| | 3 (poorly-differentiated) | 75 (60%) |
| Histological subtype (n = 143) | Serous | 64 (45%) |
| | Endometrioid | 31 (21%) |
| | Clear cell | 20 (14%) |
| | Mucinous | 13 (9%) |
| | Adenocarcinoma (unspecified) | 11 (8%) |
| | Other | 4 (3%) |
| Tumour FIGO stage (n = 142) | 1 | 48 (34%) |
| | 2 | 14 (10%) |
| | 3 | 66 (46%) |
| | 4 | 14 (10%) |
| Therapy (n = 143) | Surgery + adjuvant chemotherapy | 109 (76%) |
| | Surgery + neoadjuvant chemotherapy | 18 (13%) |
| | Surgery alone | 13 (9%) |
| | Chemotherapy alone | 3 (2%) |
| Residual disease | None | 39 (41%) |

TABLE 11

Relationship between biomarkers and tumour DNA ploidy status

| Biomarker | Diploid (n = 52) | Aneuploid (n = 91) | p-value[†] |
|---|---|---|---|
| Ki67* | 46 (33-63)[‡] | 65 (53-74) | <0.0001 |
| Mcm2* | 69 (54-83) | 86 (71-92) | <0.0001 |
| geminin* | 9 (5-16) | 16 (11-24) | <0.0001 |
| Aurora A* | 11 (5-15) | 19 (12-28) | <0.0001 |
| Aurora B* | 5 (3-9) | 11 (8-19) | <0.0001 |
| H3S10ph* | 1.1 (0.7-1.7) | 2.3 (1.6-3.6) | <0.0001 |
| Mcm2/Ki67 | 1.3 (1.1-1.7) | 1.3 (1.2-1.4) | 0.17 |
| Geminin/Ki67 | 0.23 (0.14-0.31) | 0.26 (0.18-0.34) | 0.05 |
| Aurora A/Ki67 | 0.24 (0.15-0.33) | 0.32 (0.21-0.43) | 0.01 |
| Aurora A/geminin | 1.1 (0.7-1.5) | 1.1 (0.8-1.6) | 0.61 |
| Aurora B/Ki67 | 0.12 (0.07-0.20) | 0.29 (0.13-0.27) | 0.001 |
| Aurora B/geminin | 0.55 (0.34-1.08) | 0.81 (0.46-1.05) | 0.17 |
| H3S10ph/Ki67 | 0.02 (0.02-0.04) | 0.04 (0.03-0.06) | 0.001 |

[†]Mann-Whitney test
*Labelling index (expressed as percentages)
[‡]Median (inter-quartile range)

TABLE 12

Relationship between biomarkers and tumour differentiation[Ω]

| Biomarker | Grade 1 (n = 16) | Grade 2 (n = 33) | Grade 3 (n = 75) | p-value[†] |
|---|---|---|---|---|
| Ki67* | 44 (28-49)[‡] | 54 (42-67) | 67 (49-77) | <0.0001 |
| Mcm2* | 60 (54-71) | 77 (62-86) | 87 (76-93) | <0.0001 |
| geminin* | 6 (3-13) | 11 (6-16) | 17 (10-25) | <0.0001 |
| Aurora A* | 5 (2-11) | 13 (7-21) | 19 (12-30) | <0.0001 |
| Aurora B* | 3 (1-6) | 8 (4-15) | 11 (8-19) | <0.0001 |
| H3S10ph* | 0.8 (0.6-1.7) | 1.3 (0.9-2.2) | 2.6 (1.8-3.9) | <0.0001 |
| Mcm2/Ki67 | 1.4 (1.3-1.7) | 1.3 (1.2-1.5) | 1.3 (1.1-1.4) | 0.02 |
| geminin/Ki67 | 0.18 (0.13-0.25) | 0.20 (0.14-0.32) | 0.28 (0.20-0.35) | 0.007 |
| Aurora A/Ki67 | 0.14 (0.09-0.24) | 0.26 (0.16-0.36) | 0.33 (0.21-0.44) | 0.0002 |
| Aurora A/geminin | 1.0 (0.3-1.3) | 1.1 (0.6-1.6) | 1.1 (0.8-1.6) | 0.12 |
| Aurora B/Ki67 | 0.09 (0.03-0.14) | 0.16 (0.09-0.26) | 0.20 (0.13-0.27) | 0.001 |
| Aurora B/geminin | 0.45 (0.20-0.89) | 0.64 (0.40-1.42) | 0.82 (0.46-1.05) | 0.20 |
| H3S10ph/Ki67 | 0.02 (0.01-0.04) | 0.03 (0.02-0.04) | 0.04 (0.03-0.07) | 0.0002 |

[†]Jonckheere-Terpstra test
*Labelling index (expressed as percentages)
[‡]Median (inter-quartile range)
[Ω]Nineteen (13%) of the 143 cases were not gradable.

TABLE 10-continued

Patient characteristics

| | | n (%) |
|---|---|---|
| (n = 96) | Micro | 17 (18%) |
| | <2 cm | 17 (18%) |
| | >2 cm | 23 (24%) |
| Cytology (n = 95) | Negative | 32 (34%) |
| | Positive | 63 (66%) |
| ECOG* (n = 61) (at start of first-line chemotherapy) | 0 | 49 (80%) |
| | 1 | 7 (11%) |
| | 2 | 1 (2%) |
| | 3 | 3 (5%) |
| | 4 | 1 (2%) |
| CA125 response (n = 95) (at end of first-line chemotherapy) | <35 | 82 (86%) |
| | >35 | 13 (14%) |

*Performance status

TABLE 13

Relationship between biomarkers and tumour stage[Ω]

| Biomarker | Stage 1 (n = 48) | Stages 2, 3, 4 (n = 94) | p-value[†] |
|---|---|---|---|
| Ki67* | 52 (43-69)[‡] | 62 (43-72) | 0.20 |
| Mcm2* | 76 (60-86) | 82 (68-91) | 0.11 |
| geminin* | 12 (8-17) | 16 (8-24) | 0.10 |
| Aurora A* | 12 (6-20) | 17 (11-27) | 0.006 |
| Aurora B* | 7 (4-12) | 10 (4-17) | 0.06 |
| H3S10ph* | 1.3 (0.8-2.2) | 2.2 (1.3-3.5) | 0.002 |
| Mcm2/Ki67 | 1.3 (1.1-1.5) | 1.3 (1.1-1.5) | 0.39 |
| geminin/Ki67 | 0.24 (0.16-0.30) | 0.25 (0.18-0.36) | 0.24 |
| Aurora A/Ki67 | 0.21 (0.15-0.33) | 0.30 (0.19-0.43) | 0.003 |
| Aurora A/geminin | 1.0 (0.6-1.4) | 1.2 (0.8-1.6) | 0.04 |
| Aurora B/Ki67 | 0.14 (0.08-0.22) | 0.17 (0.11-0.26) | 0.13 |
| Aurora B/geminin | 0.75 (0.40-1.02) | 0.68 (0.37-1.07) | 0.76 |
| H3S10ph/Ki67 | 0.03 (0.02-0.04) | 0.04 (0.02-0.06) | 0.005 |

[†]Mann-Whitney test
*Labelling index (expressed as percentages)
[‡]Median (inter-quartile range)
[Ω]One case was excluded from the analysis because of missing stage information.

TABLE 14

Relationship between biomarkers and disease-free survival

| Biomarker | Hazard Ratio (95% CI) | p-value† |
|---|---|---|
| Ki67* | 1.07 (0.95 to 1.22) | 0.25 |
| Mcm2* | 1.13 (0.98 to 1.29) | 0.09 |
| geminin* | 1.17 (0.93 to 1.47) | 0.19 |
| Aurora A* | 1.29 (1.06 to 1.58) | 0.01 |
| Aurora B* | 1.19 (0.95 to 1.49) | 0.13 |
| H3S10ph° | 1.76 (1.08 to 2.88) | 0.02 |
| Mcm2/Ki67^ | 0.79 (0.45 to 1.41) | 0.42 |
| geminin/Ki67^ | 1.09 (0.90 to 1.32) | 0.38 |
| Aurora A/Ki67^ | 1.20 (1.06 to 1.36) | 0.004 |
| Aurora A/geminin | 1.23 (0.97 to 1.56) | 0.09 |
| Aurora B/Ki67^ | 1.22 (1.03 to 1.45) | 0.02 |
| Aurora B/geminin | 1.38 (0.98 to 1.96) | 0.07 |
| H3S10ph/Ki67° | 1.58 (0.96 to 2.57) | 0.07 |

†Log-rank test
*Hazard Ratios refer to an absolute increase of 10% in the biomarker percentage.
^Hazard Ratios refer to an absolute increase of 0.1 in the ratio.
°Variables were highly skewed and therefore split into two categories at the median value (1.99 for H3S10ph, 0.032 for H3S10ph/Ki67). Hazard ratios are for the high group compared to the low group for each variable.
For other variables hazard ratios refer to an increase of 1 unit.

TABLE 15

Relationship between cell cycle phenotype and clinicopathological parameters.

| | I (Out-of-cycle) Mcm2 < 30% N = 33 (18%) | II (In cycle G1 delayed/arrested) Mcm2 ≧ 30% geminin < 7% N = 44 (24%) | III (Actively cycling) Mcm2 ≧ 30% geminin ≧ 7% N = 105 (58%) |
|---|---|---|---|
| Age - mean (sd) p = 0.13) | 61.9 (12.4) | 61.2 (24.1) | 57.4 (15.9) |
| Grade (p < 0.001)* | | | |
| 1 | 27% (9.33) | 23% (10.44) | 5% (5.105) |
| 2 | 61% (20.33) | 64% (28.44) | 30% (32.105) |
| 3 | 12% (4.33) | 14% (6.44) | 65% (68.105) |
| Size - mean (sd) (p = 0.55) | 24.7 (17.5) | 29.1 (19.8) | 28.0 (17.4) |
| Positive Nodes (p = 0.23) | 39% (12.31) | 35% (13.40) | 48% (47.98) |
| NPI - mean (sd) (p = 0.001) | 3.8 (1.3) | 4.0 (1.2) | 4.9 (1.2) |
| ER - ve cases* (p = 0.08) | 100% (78.9% to 100%) | 100% (100% to 100%) | 88.9% (0% to 100%) |
| PR - ve cases* (p = 0.14) | 72.4% (35.8% to 100%) | 92.2% (47% to 100%) | 18.8% (0% to 97.8%) |
| Her-2 | | | |
| 0 | 66.7% (22.33) | 68.2% (30.44) | 53.3% (56.105) |
| 1- | 15.2% (5.33) | 18% (8.44) | 19% (20.105) |
| 2- | 9.1% (3.33) | 4.5% (2.44) | 7.6% (8.105) |
| 3- | 9.1% (3.33) | 9.1% (4.44) | 20% (21.105) |
| (p = 0.45) | | | |

†Median (interquartile ranges)
*Significant association restricted to phenotype III

The invention claimed is:

1. A method for treating a subject having cancer, the method comprising the steps of:
   (a) assessing a level of Mcm2 in a biological sample from the subject; and
   (b) assessing a level of geminin in the biological sample from the subject,
   wherein the combination of the level of the Mcm2 compared to a pre-determined value and the level of the geminin compared to a predetermined value is indicative of the treatment regimen prescribed for the subject; and
   (c) treating the subject with a treatment regimen comprising:
      (i) administering one or more non-cell cycle phase-specific chemotherapeutic agents if the level of the Mcm2 compared to a pre-determined value is low and the level of the geminin compared to a pre-determined value is low; or
      (ii) administering one or more G1 phase-specific chemotherapeutic agents to the subject, or administering one or more non-S and non-G2/M cell cycle phase-specific chemotherapeutic agents to the subject, if the level of the Mcm2 compared to a pre-determined value is high and the level of the geminin compared to a pre-determined value is low; or
      (iii) conducting surgery on the subject, or administering one or more S cell cycle phase-specific chemotherapeutic agents or G2/M cell cycle phase-specific chemotherapeutic agents to the subject, if the level of the Mcm2 compared to a pre-determined value is high and the level of the geminin compared to a pre-determined value is high.

2. The method of claim 1, further comprising assessing a level of a third biomarker in the biological sample from the subject, wherein the third biomarker is H3 S10ph.

3. The method of claim 1, further comprising assessing the level of a third biomarker selected from at least one of Aurora A, Plk1 and H3S10ph in the biological sample from said subject.

4. The method of claim 1, wherein the biological sample is tumor biopsy tissue.

5. The method of claim 1, wherein the level of the Mcm2 and geminin is measured using an immunological assay method.

6. The method of claim 5, wherein the immunological assay method is selected from the group consisting of immunohistochemistry, immunocytochemistry, dot blot analysis, slot blot analysis, RIA, peptide microarray, Western blot, and ELISA.

7. The method of claim 1, wherein the subject has breast cancer or prostate cancer.

8. The method of claim 1, wherein the Mcm2 and geminin are assessed concurrently.

9. The method of claim 1, wherein the level of the Mcm2 is assessed before assessing the level of the geminin.

10. The method of claim 1, wherein the assessing of a) and b) comprises contacting the sample with an antibody directed to Mcm2 and contacting the sample with an antibody directed to the geminin, simultaneously or consecutively.

11. The method of claim 1, further comprising obtaining the biological sample from the subject prior to said assessing of (a) and (b).

* * * * *

UNITED STATES PATENT AND TRADEMARK OFFICE
CERTIFICATE OF CORRECTION

Page 1 of 1

PATENT NO.        : 8,512,716 B2
APPLICATION NO.   : 12/738062
DATED             : August 20, 2013
INVENTOR(S)       : Kai Stoeber and Gareth Hayden Williams It is certified that error appears in the above-identified patent and that said Letters Patent is hereby corrected as shown below:

In the Claims

Column 40,
Line 34, "H3 S10ph" should read --H3S10ph--

Signed and Sealed this
Fifth Day of November, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,512,716 B2  Page 1 of 1
APPLICATION NO. : 12/738062
DATED : August 20, 2013
INVENTOR(S) : Stoeber et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 271 days.

Signed and Sealed this

Fifteenth Day of September, 2015

Michelle K. Lee
*Director of the United States Patent and Trademark Office*